US012678308B2

(12) United States Patent
Ni Ghriallais et al.

(10) Patent No.: US 12,678,308 B2
(45) Date of Patent: Jul. 14, 2026

(54) DEVICE AND METHOD FOR DEPLOYING EXPANDABLE IMPLANTS

(71) Applicant: ProVerum Limited, Dublin (IE)

(72) Inventors: Riona Ni Ghriallais, Gaillimh (IE); Conor Harkin, Dublin (IE)

(73) Assignee: ProVerum Limited, Dublin (IE)

( * ) Notice: Subject to any disclaimer, the term of this patent is extended or adjusted under 35 U.S.C. 154(b) by 0 days.

(21) Appl. No.: 18/649,697

(22) Filed: Apr. 29, 2024

(65) Prior Publication Data

US 2024/0358535 A1     Oct. 31, 2024

Related U.S. Application Data

(63) Continuation of application No. PCT/EP2024/061319, filed on Apr. 24, 2024.

(30) Foreign Application Priority Data

Apr. 27, 2023   (GB) ...................................... 2306224
Apr. 27, 2023   (GB) ...................................... 2306227

(51) Int. Cl.
   *A61F 2/966*     (2013.01)
   *A61F 2/04*     (2013.01)
(52) U.S. Cl.
   CPC ........ *A61F 2/966* (2013.01); *A61F 2002/047* (2013.01); *A61F 2002/9665* (2013.01)
(58) Field of Classification Search
   CPC ................ A61F 2/996; A61F 2002/047; A61F 2002/9665
   See application file for complete search history.

(56) References Cited

U.S. PATENT DOCUMENTS 4,580,568 A     4/1986   Gianturco
4,830,003 A     5/1989   Wolff et al.
        (Continued)

FOREIGN PATENT DOCUMENTS

BE          892016      5/1982
BE         1015962     12/2005
        (Continued)

OTHER PUBLICATIONS

Combined Search and Examination Report issued in GB Application No. GB2306224.3, dated Oct. 11, 2023.
        (Continued)

*Primary Examiner* — Jerrah Edwards
*Assistant Examiner* — Aren Patel
(74) *Attorney, Agent, or Firm* — Knobbe, Martens, Olson & Bear, LLP

(57) ABSTRACT

A system for deploying an implant in a patient's body comprises a deployment drive that is operable by moving a deployment control element from a first position in which the implant is undeployed, to a second position in which the implant is partially deployed, and to a third position in which the implant is fully deployed. A detent mechanism blocks movement of the control element from the second position to the third position and comprises a follower that is movable into a deployment stop position by moving the control element from the first position to the second position, hence blocking movement of the control element into the third position. A detent release element is movable into an unlock position, that movement moving the follower from the deployment stop position into a deployment release position that frees the control element for movement from the second position to the third position.

20 Claims, 24 Drawing Sheets

(56)                    References Cited

U.S. PATENT DOCUMENTS

| | | | |
|---|---|---|---|
| 5,035,706 A | 7/1991 | Giantureo et al. | |
| 5,159,920 A | 11/1992 | Condon et al. | |
| 5,269,802 A | 12/1993 | Garber | |
| 5,292,331 A | 3/1994 | Boneau | |
| 5,591,277 A | 1/1997 | Braunheim | |
| 5,599,325 A | 2/1997 | Ju et al. | |
| 5,674,278 A | 10/1997 | Boneau | |
| 5,697,967 A | 12/1997 | Dinh et al. | |
| 5,782,838 A | 7/1998 | Beyar et al. | |
| 5,830,179 A | 11/1998 | Mikus et al. | |
| 6,090,063 A | 7/2000 | Makower et al. | |
| 6,093,194 A | 7/2000 | Mikus et al. | |
| 6,110,199 A | 8/2000 | Walak | |
| 6,248,058 B1 | 6/2001 | Silverman et al. | |
| 6,395,017 B1 | 5/2002 | Dwyer et al. | |
| 6,929,663 B2 | 8/2005 | Rioux et al. | |
| 7,112,226 B2 | 9/2006 | Gellman | |
| 7,611,528 B2 | 11/2009 | Goodson, IV et al. | |
| 7,645,286 B2 | 1/2010 | Catanese, III et al. | |
| 7,758,594 B2 | 7/2010 | Lamson et al. | |
| 7,766,923 B2 | 8/2010 | Catanese, III et al. | |
| 7,780,682 B2 | 8/2010 | Catanese, III et al. | |
| 8,070,825 B2 | 12/2011 | Devonec | |
| 8,287,602 B2 | 10/2012 | Daignault et al. | |
| 8,491,606 B2 | 7/2013 | Tong et al. | |
| 8,591,569 B2 | 11/2013 | Shin et al. | |
| 8,603,187 B2 | 12/2013 | Kilemnik et al. | |
| 8,702,788 B2 | 4/2014 | Kheradvar et al. | |
| 8,715,239 B2 | 5/2014 | Lamson et al. | |
| 8,926,494 B1 | 1/2015 | Cook et al. | |
| 9,005,183 B2 | 4/2015 | Harkins, Jr. | |
| 9,114,039 B2 | 8/2015 | Jordan et al. | |
| 9,333,102 B2 | 5/2016 | Yachia et al. | |
| 9,402,711 B2 | 8/2016 | Catanese, III et al. | |
| 9,517,120 B2 | 12/2016 | Devonec | |
| 9,775,698 B2 | 10/2017 | Herrera et al. | |
| 9,848,905 B2 | 12/2017 | Kilemnik | |
| 9,931,192 B2 | 4/2018 | McLean et al. | |
| 9,950,138 B2 | 4/2018 | O'Callaghan et al. | |
| 9,968,479 B2 | 5/2018 | Harkins, Jr. | |
| 10,004,584 B2 | 6/2018 | Bartning et al. | |
| 10,035,005 B2 | 7/2018 | Bar-On et al. | |
| 10,058,718 B2 | 8/2018 | Sethuraman et al. | |
| 10,105,132 B2 | 10/2018 | Lamson et al. | |
| 10,130,353 B2 | 11/2018 | Catanese, III et al. | |
| 10,292,801 B2 | 5/2019 | Lamson et al. | |
| 10,406,333 B2 | 9/2019 | Feld | |
| 10,478,283 B2 | 11/2019 | Bachar | |
| 10,507,122 B2 | 12/2019 | Bachar | |
| 10,682,245 B2 | 6/2020 | Harkin et al. | |
| 10,743,975 B2 | 8/2020 | Herrera et al. | |
| 10,881,539 B2 | 1/2021 | Harkin et al. | |
| 10,912,637 B2 | 2/2021 | Lamson et al. | |
| 10,952,885 B2 | 3/2021 | Sicotte et al. | |
| 11,027,106 B2 | 6/2021 | Bachar | |
| 11,090,036 B2 | 8/2021 | Lamson et al. | |
| 11,096,774 B2 | 8/2021 | Sicotte et al. | |
| 11,241,312 B2 | 2/2022 | Simonin | |
| 11,273,025 B2 | 3/2022 | Ni Ghriallais et al. | |
| 11,278,293 B2 | 3/2022 | Mantri et al. | |
| 11,304,724 B2 | 4/2022 | Kilemnik | |
| 11,484,398 B2 | 11/2022 | Ni Ghriallais et al. | |
| 11,497,637 B2 | 11/2022 | Huang et al. | |
| 11,547,546 B2 | 1/2023 | Hsu et al. | |
| 11,571,290 B2 | 2/2023 | Bachar | |
| 11,602,621 B2 | 3/2023 | Ni Ghriallais et al. | |
| 11,690,702 B2 | 7/2023 | Kadron et al. | |
| 11,724,076 B2 | 8/2023 | Feld | |
| 11,738,184 B2 | 8/2023 | Bachar | |
| 11,771,575 B2 | 10/2023 | Bly et al. | |
| 11,812,930 B2 | 11/2023 | Jen et al. | |
| 11,813,184 B2 | 11/2023 | Sicotte et al. | |
| 11,850,140 B2 | 12/2023 | Lamson et al. | |
| 11,890,213 B2 | 2/2024 | Bly et al. | |
| 11,903,859 B1 | 2/2024 | Sicotte et al. | |
| 11,925,376 B2 | 3/2024 | Golan et al. | |
| 11,969,183 B2 | 4/2024 | Kilemnik | |
| 11,998,438 B2 | 6/2024 | Sicotte et al. | |
| 12,042,372 B2 | 7/2024 | Lamson et al. | |
| 12,076,226 B2 | 9/2024 | Bachar | |
| 12,090,040 B2 | 9/2024 | Sicotte et al. | |
| 12,121,228 B2 | 10/2024 | Lamson et al. | |
| 12,171,650 B2 | 12/2024 | Ni Ghriallais et al. | |
| 12,193,956 B2 | 1/2025 | Koroschetz et al. | |
| 12,251,298 B2 | 3/2025 | Kilemnik | |
| 12,268,411 B2 | 4/2025 | Kilemnik | |
| 12,296,123 B2 | 5/2025 | Feld | |
| 12,324,576 B2 | 6/2025 | Catanese, III et al. | |
| 12,329,663 B2 | 6/2025 | Harkin et al. | |
| 12,357,479 B2 | 7/2025 | Kadlec et al. | |
| 12,376,842 B2 | 8/2025 | Catanese, III et al. | |
| 12,383,288 B2 | 8/2025 | Jen et al. | |
| 12,390,320 B2 | 8/2025 | Ni Ghriallais et al. | |
| 2001/0027323 A1* | 10/2001 | Sullivan, III | A61F 2/95 606/108 |
| 2002/0007206 A1 | 1/2002 | Bui | |
| 2002/0007222 A1 | 1/2002 | Desai | |
| 2002/0035391 A1 | 3/2002 | Mikus et al. | |
| 2002/0156394 A1 | 10/2002 | Mehrotra et al. | |
| 2004/0107004 A1 | 6/2004 | Levine et al. | |
| 2004/0167635 A1 | 8/2004 | Yachia et al. | |
| 2006/0100688 A1 | 5/2006 | Jordan et al. | |
| 2006/0136031 A1 | 6/2006 | Gallo et al. | |
| 2006/0155366 A1 | 7/2006 | LaDuca et al. | |
| 2006/0247724 A1 | 11/2006 | Gerber et al. | |
| 2006/0276871 A1 | 12/2006 | Lamson et al. | |
| 2006/0287674 A1* | 12/2006 | Ginn | A61B 17/083 606/221 |
| 2007/0077266 A1 | 4/2007 | Egashira | |
| 2007/0163668 A1 | 7/2007 | Arbefeuille et al. | |
| 2007/0255390 A1 | 11/2007 | Ducke et al. | |
| 2008/0077227 A1 | 3/2008 | Oullette et al. | |
| 2008/0255651 A1 | 10/2008 | Dwork | |
| 2009/0171442 A1 | 7/2009 | Young et al. | |
| 2009/0210045 A1 | 8/2009 | Sorensen et al. | |
| 2009/0312667 A1 | 12/2009 | Utsunomiya et al. | |
| 2010/0137893 A1 | 6/2010 | Kilemnick et al. | |
| 2010/0152835 A1 | 6/2010 | Orr | |
| 2011/0040312 A1 | 2/2011 | Lamson et al. | |
| 2011/0301690 A1 | 12/2011 | Giasolli | |
| 2011/0307049 A1 | 12/2011 | Kao | |
| 2012/0179086 A1 | 7/2012 | Shank | |
| 2012/0238803 A1 | 9/2012 | Lund | |
| 2012/0290065 A1 | 11/2012 | Li et al. | |
| 2014/0012192 A1 | 1/2014 | Bar-On et al. | |
| 2014/0188249 A1 | 7/2014 | Pendleton et al. | |
| 2014/0257020 A1 | 9/2014 | Smith et al. | |
| 2015/0257908 A1 | 9/2015 | Chao et al. | |
| 2015/0374408 A1 | 12/2015 | Ogdahl et al. | |
| 2016/0007987 A1 | 1/2016 | Catanese, III et al. | |
| 2016/0262862 A1 | 9/2016 | Fischer | |
| 2016/0317180 A1 | 11/2016 | Kilemnik | |
| 2016/0361088 A1* | 12/2016 | Maguire | A61B 17/3415 |
| 2017/0135830 A1 | 5/2017 | Harkin et al. | |
| 2017/0165062 A1 | 6/2017 | Rothstein | |
| 2018/0028222 A1 | 2/2018 | Kilemnik | |
| 2018/0153693 A1 | 6/2018 | Copeland et al. | |
| 2018/0221055 A1* | 8/2018 | Grace | A61L 31/10 |
| 2018/0235651 A1 | 8/2018 | Kilemnik | |
| 2018/0256375 A1 | 9/2018 | Sennes et al. | |
| 2018/0256848 A1* | 9/2018 | Ramanathan | A61M 25/09 |
| 2018/0280669 A1 | 10/2018 | Shlomovitz et al. | |
| 2018/0318114 A1 | 11/2018 | Huang et al. | |
| 2018/0325705 A1 | 11/2018 | Harkin et al. | |
| 2018/0344995 A1 | 12/2018 | Bar-On et al. | |
| 2019/0046207 A1 | 2/2019 | Czernik et al. | |
| 2019/0262592 A1 | 8/2019 | Bachar | |
| 2019/0295444 A1 | 9/2019 | Zunke et al. | |
| 2019/0298334 A1 | 10/2019 | Catanese, III et al. | |
| 2020/0022692 A1 | 1/2020 | Lamson et al. | |
| 2020/0038213 A1 | 2/2020 | Bly et al. | |
| 2020/0315823 A1 | 10/2020 | Harkin et al. | |
| 2020/0323618 A1 | 10/2020 | Bly et al. | |
| 2020/0345524 A1* | 11/2020 | Collins | A61F 2/95 |

(56) References Cited

U.S. PATENT DOCUMENTS

| | | |
|---|---|---|
| 2020/0368008 A1 | 11/2020 | Koroschetz |
| 2021/0022594 A1 | 1/2021 | Jen et al. |
| 2021/0038387 A1 | 2/2021 | Zhang et al. |
| 2021/0052854 A1 | 2/2021 | Tavallaei et al. |
| 2021/0059704 A1 | 3/2021 | Kilemnik |
| 2021/0100666 A1 | 4/2021 | Harkin et al. |
| 2021/0106730 A1 | 4/2021 | Koroschetz et al. |
| 2021/0145619 A1 | 5/2021 | Bly et al. |
| 2021/0154000 A1 | 5/2021 | Ni Ghriallais et al. |
| 2021/0161642 A1 | 6/2021 | Jen et al. |
| 2021/0259799 A1 | 8/2021 | Lessard et al. |
| 2021/0290917 A1 | 9/2021 | Bachar |
| 2021/0307942 A1 | 10/2021 | Flora et al. |
| 2022/0054184 A9 | 2/2022 | Rajagopalan et al. |
| 2022/0079613 A1 | 3/2022 | Aljuri et al. |
| 2022/0096113 A1 | 3/2022 | Kilemnik |
| 2022/0110737 A1 | 4/2022 | Mehta et al. |
| 2022/0133462 A1 | 5/2022 | Kilemnik |
| 2022/0167921 A1 | 6/2022 | Aljuri et al. |
| 2022/0192813 A1 | 6/2022 | Ni Ghriallais et al. |
| 2022/0273918 A1* | 9/2022 | Ni Ghriallais ........ A61M 29/00 |
| 2022/0296291 A1 | 9/2022 | Anderson et al. |
| 2022/0361886 A1 | 11/2022 | Widenhouse et al. |
| 2022/0387199 A1 | 12/2022 | Chu |
| 2022/0395363 A1 | 12/2022 | Ni Ghriallais et al. |
| 2023/0025085 A1 | 1/2023 | Ni Ghriallais et al. |
| 2023/0046007 A1 | 2/2023 | Bauer et al. |
| 2023/0092775 A1 | 3/2023 | Juan et al. |
| 2023/0181302 A1 | 6/2023 | Jürgens et al. |
| 2023/0181303 A1 | 6/2023 | Jürgens et al. |
| 2023/0181304 A1 | 6/2023 | Jürgens et al. |
| 2023/0181884 A1 | 6/2023 | Ni Ghriallais et al. |
| 2023/0225606 A1 | 7/2023 | Burdulis et al. |
| 2023/0240829 A1 | 8/2023 | Heftman et al. |
| 2024/0033067 A1 | 2/2024 | Bachar |
| 2024/0108868 A1 | 4/2024 | Brockmann et al. |
| 2024/0115405 A1 | 4/2024 | Kadlec et al. |
| 2024/0130843 A1 | 4/2024 | Howes |
| 2024/0225813 A1 | 7/2024 | Kadlec et al. |
| 2024/0225871 A1 | 7/2024 | Sicotte et al. |
| 2024/0293215 A1 | 9/2024 | Mehta et al. |
| 2024/0299153 A1 | 9/2024 | Schulz et al. |
| 2024/0315825 A1 | 9/2024 | Bly et al. |
| 2024/0335274 A1 | 10/2024 | Wu et al. |
| 2024/0341984 A1 | 10/2024 | Bly et al. |
| 2024/0358493 A1 | 10/2024 | Lamson et al. |
| 2024/0358534 A1 | 10/2024 | Ni Ghriallais et al. |
| 2024/0374368 A1 | 11/2024 | Bachar |
| 2025/0032111 A1 | 1/2025 | Lamson et al. |
| 2025/0114225 A1 | 4/2025 | Bly et al. |
| 2025/0143902 A1 | 5/2025 | Koroschetz et al. |
| 2025/0152927 A1 | 5/2025 | Kilemnik |
| 2025/0204948 A1 | 6/2025 | Kilemnik |
| 2025/0213347 A1 | 7/2025 | Kilemnik |
| 2025/0213376 A1 | 7/2025 | Ni Ghriallais et al. |
| 2025/0221810 A1 | 7/2025 | Sicotte et al. |
| 2025/0255642 A1 | 8/2025 | Kilemnik |

FOREIGN PATENT DOCUMENTS

| | | |
|---|---|---|
| CN | 101945621 | 1/2011 |
| CN | 202822454 | 3/2013 |
| EP | 1 420 720 | 9/2007 |
| EP | 1 599 153 | 11/2010 |
| EP | 1 959 876 | 9/2011 |
| EP | 1 827 305 | 1/2012 |
| EP | 2 446 855 | 5/2012 |
| EP | 2 316 392 | 1/2013 |
| EP | 1887970 | 4/2016 |
| EP | 2160151 | 4/2016 |
| EP | 3 167 845 | 5/2017 |
| EP | 2370029 | 5/2018 |
| EP | 2685933 | 2/2019 |
| EP | 3089780 | 9/2019 |
| EP | 3 610 831 | 2/2020 |
| EP | 2658458 | 2/2020 |
| EP | 2408506 | 9/2020 |
| EP | 3581232 | 2/2021 |
| EP | 3096711 | 3/2021 |
| EP | 2967819 | 4/2021 |
| EP | 3328317 | 10/2022 |
| EP | 3445284 | 5/2023 |
| EP | 3373854 | 7/2023 |
| EP | 3415121 | 9/2023 |
| EP | 3618914 | 10/2023 |
| EP | 3658081 | 2/2024 |
| EP | 3116583 | 3/2024 |
| EP | 3393372 | 6/2024 |
| EP | 2866876 | 8/2024 |
| EP | 3826584 | 8/2024 |
| EP | 4161626 | 8/2024 |
| EP | 3831342 | 9/2024 |
| EP | 4431057 | 9/2024 |
| EP | 4061200 | 11/2024 |
| EP | 3793476 | 1/2025 |
| EP | 3773270 | 2/2025 |
| EP | 4061292 | 3/2025 |
| EP | 3597148 | 4/2025 |
| EP | 4041128 | 7/2025 |
| EP | 4599777 | 8/2025 |
| FR | 2586185 | 2/1987 |
| JP | 51-51894 | 5/1976 |
| JP | 2005-261686 | 9/2005 |
| WO | WO 90/13332 | 11/1990 |
| WO | WO 2011/021779 | 2/2011 |
| WO | WO 2011/002779 | 6/2011 |
| WO | WO 2015/101975 | 7/2015 |
| WO | WO 2015/111063 | 7/2015 |
| WO | WO 2015/138763 | 9/2015 |
| WO | WO 2017/081326 | 5/2017 |
| WO | WO 2018/107123 | 6/2018 |
| WO | WO 2019/222481 | 11/2019 |
| WO | WO 2021/099646 | 5/2021 |
| WO | WO 2021/113340 | 6/2021 |
| WO | WO 2023/004362 | 1/2023 |
| WO | WO 2023/191688 | 10/2023 |
| WO | WO 2024/003851 | 1/2024 |
| WO | WO 2024/035435 | 2/2024 |
| WO | WO 2024/064905 | 3/2024 |
| WO | WO 2024/161403 | 8/2024 |
| WO | WO 2024/194788 | 9/2024 |
| WO | WO 2024/211119 | 10/2024 |
| WO | WO 2024/217170 | 10/2024 |
| WO | WO 2024/217171 | 10/2024 |
| WO | WO 2025/036411 | 2/2025 |
| WO | WO 2025/036412 | 2/2025 |
| WO | WO 2025/045068 | 3/2025 |
| WO | WO 2025/071553 | 4/2025 |
| WO | WO 2025/103935 | 5/2025 |

OTHER PUBLICATIONS

Combined Search and Examination Report issued in GB Application No. GB2306227.6, dated Oct. 11, 2023.
International Search Report and Written Opinion issued in PCT Application No. PCT/EP2024/061318, dated Jul. 31, 2024. (5WO).
International Search Report and Written Opinion issued in PCT Application No. PCT/EP2024/061319, dated Jul. 31, 2024. (6WO).
U.S. Appl. No. 15/351,282 (U.S. Pat. No. 10,682,245), filed Nov. 14, 2016 (Jun. 16, 2020), Implantable Biocompatible Expander Suitable for Treatment of Constrictions of Body Lumen.
U.S. Appl. No. 16/856,637, filed Apr. 23, 2020, Implantable Biocompatible Expander Suitable for Treatment of Constrictions of Body Lumen.
U.S. Appl. No. 15/775,257 (U.S. Pat. No. 10,881,539), filed May 10, 2018 (Jan. 5, 2021), An Implantable Biocompatible Expander Suitable for Treatment of Constrictions of Body Lumen.
U.S. Appl. No. 17/109,003, filed Dec. 1, 2020, Implantable Biocompatible Expander Suitable for Treatment of Constrictions of Body Lumen.
U.S. Appl. No. 16/692,347 (U.S. Pat. No. 11,273,025), filed Nov. 22, 2019 (Mar. 15, 2022), Expandable Implant Delivery Device.

(56)     References Cited

OTHER PUBLICATIONS

U.S. Appl. No. 17/654,642 (U.S. Pat. No. 11,484,398), filed Mar. 14, 2022 (Nov. 1, 2022), Implant Delivery Methods.
U.S. Appl. No. 17/958,689, filed Oct. 3, 2022, Implant Delivery Methods.
U.S. Appl. No. 17/777,583, filed May 17, 2022, Device for Viewing and Deploying Expandable Implants.
U.S. Appl. No. 17/663,812 (U.S. Pat. No. 11,602,621), filed May 17, 2022 (Mar. 14, 2023), Device for Controllably Deploying Expandable Implants.
U.S. Appl. No. 18/107,429, filed Feb. 8, 2023, Device for Controllably Deploying Expandable Implants.
U.S. Appl. No. 18/649,702, filed Apr. 29, 2024, Device and Method for Deploying Expandable Implants.
U.S. Appl. No. 18/649,697, filed Apr. 29, 2024, Device and Method for Deploying Expandable Implants.

* cited by examiner

DEVICE AND METHOD FOR DEPLOYING EXPANDABLE IMPLANTS

INCORPORATION BY REFERENCE TO ANY PRIORITY APPLICATIONS

This application is a continuation of PCT/EP2024/061319, filed Apr. 24, 2024 and titled "Device and Method For Deploying Expandable Implants" which claims the benefit of priority to GB Patent Application No. GB2306224.3, filed Apr. 27, 2023 and titled "Device and Method For Deploying Expandable Implants" and GB Patent Application No. GB2306227.6, filed Apr. 27, 2023 and titled "Device and Method For Deploying Expandable Implants", each of which is incorporated in its entirety by reference herein. Any and all applications for which a foreign or domestic priority claim is identified in the Application Data Sheet as filed with the present application are hereby incorporated by reference under 37 CFR 1.57.

FIELD OF THE INVENTION

The present disclosure relates to a delivery device for an expandable implant and to a method for using such a device. In particular, but not exclusively, such a delivery device provides solutions to deploy a self-expanding implant or expander to dilate the prostatic urethra of a patient, thereby to treat conditions such as benign prostatic hyperplasia (BPH). Certain aspects and embodiments of the invention therefore relate to a delivery device for locating an expandable implant, such as within the prostatic urethra to treat BPH, and to a method of delivering or deploying such an implant.

BPH is a noncancerous disease that results in enlargement of the prostate. The prostate surrounds a section of the urethra adjoining the bladder, namely the prostatic urethra. Thus, as the prostate expands, it tends to press inwardly against the prostatic urethra and the neck of the bladder, making it difficult for a patient to pass urine.

In the US alone, more than US$5 billion is spent annually on medication to manage BPH. It is also known to treat BPH using various surgical techniques. However, certain surgical solutions can be particularly invasive and uncomfortable for the patient.

SUMMARY OF THE INVENTION

There has been a move toward the use of expandable implants or stents that can be inserted into the prostatic urethra to react against inward pressure that may be applied to the urethra and bladder neck by an enlarged prostate.

Expandable implants provide a minimally invasive and low-cost solution for treating BPH. However, locating the implant in the correct position within the urethra is essential but can be challenging for a clinician. If the implant is deployed incorrectly, it may not provide adequate symptom relief, could fail due to migration or excessive encrustation and can be challenging and invasive to recover from the urethra after deployment.

Various examples of expanders for treating BPH are disclosed in WO 2017/081326, which is incorporated in its entirety by reference herein. The expanders of WO 2017/081326 are designed to be positioned, for example, within the prostatic urethra between the bladder neck and the external sphincter and then to self-expand laterally. The expander thereby applies, in one embodiment, a radially-outward force on the surrounding walls of the prostatic urethra to alleviate the symptoms of BPH.

Deploying an expander correctly within the prostatic urethra involves having the expander positioned accurately both in a longitudinal direction and circumferentially or angularly in several embodiments. In particular, the expander may be positioned longitudinally at a position between the bladder neck and the external sphincter and may also be oriented so as to engage the three lobes of the prostate. Incorrect deployment is likely if the expander is deployed accidentally or prematurely or if the clinician cannot properly visualise the structures surrounding the prostatic urethra before deployment.

If an expander is deployed in an incorrect position or orientation, an adverse outcome is possible and a complex procedure may be required to remove or reposition the expander. As a result, there is a need for a minimally-invasive delivery device that allows a clinician accurately to position and deploy an expandable implant within the prostatic urethra of a patient.

WO 2017/081326 describes embodiments of a device for delivering an expander to a target site within a body lumen such as the prostatic urethra. In several embodiments, the delivery device comprises an ejection element with a triangular cross-section configured to engage and support the expander. A delivery tube of the delivery device may be inserted into the penile urethra and its distal end may be advanced along the urethra to a target site in the prostatic urethra. When the clinician is satisfied that the expander is in the correct position both longitudinally and in angular orientation relative to the lobes of the prostate, the ejection element can be advanced distally to eject the expander from within a surrounding sheath of the delivery tube.

Certain single-step delivery devices may benefit from some refinements in practice. For example, a single-step delivery device may be susceptible to accidental or premature deployment. Also, some single-step delivery devices may not ideally enable visual verification of the correct position of the expander relative to the surrounding anatomy before the clinician must decide whether to deploy the expander. Furthermore, unless a clinician withdraws a delivery tube of a single-step delivery device proximally while advancing the ejection element distally, the expander could spring or jump forward upon deployment. Unhelpfully, this might tend to alter the position of the expander in the prostatic urethra, both longitudinally and circumferentially, as a consequence of the deployment action. In this respect, relying on the expander to self-locate relative to the anatomy may be unreliable and unpredictable.

WO 2021/099646, which is incorporated in its entirety by reference herein, discloses embodiments of improved delivery devices for deploying an expander within the prostatic urethra. Among its improvements, WO 2021/099646 discloses provisions to prevent inadvertent deployment of the expander; to improve visualization of the expander relative to the surrounding anatomy before deployment; and to pause or reverse deployment if a clinician determines that the expander could otherwise be positioned incorrectly at the target site. WO 2021/099646 also discloses provisions to steer the delivery tube along the penile urethra to the target site.

Embodiments of the present invention provide elegant, compact, effective and reliable solutions for operation of a detent mechanism and for driving and controlling differential longitudinal movement of concentric elements of the delivery tube during in situ visualisation and deployment. As a result, several embodiments of the invention provide an ergonomically-designed delivery device that allows an implant to be deployed accurately with simple, safe, and largely one-handed operation.

In several embodiments, the invention may be expressed as a deployment system for deploying an implant in a patient's body, the system comprising: a deployment drive that is operable in response to movement of a deployment control element from a first position in which the implant is undeployed, to a second position in which the implant is partially deployed, and to a third position in which the implant is fully deployed; and a detent mechanism that is configured to block movement of the deployment control element from the second position to the third position, wherein the detent mechanism comprises: a follower that is movable into a deployment stop position by movement of the deployment control element from the first position to the second position, hence blocking further movement of the deployment control element into the third position; and a detent release element that is movable into an unlock position, said movement of the detent release element acting on the follower to move the follower from the deployment stop position into a deployment release position that frees the deployment control element for movement from the second position to the third position. The detent release element could, for example, adjoin the deployment control element.

In one embodiment, a deployment system for deploying an implant in a patient's body comprises: a deployment drive that is operable in response to movement of a deployment control element from a first position in which the implant is undeployed, to a second position in which the implant is partially deployed, and to a third position in which the implant is fully deployed; and a detent mechanism that is configured to block movement of the deployment control element from the second position to the third position, wherein the detent mechanism comprises: a follower that is movable into a deployment stop position by movement of the deployment control element from the first position to the second position, thereby blocking further movement of the deployment control element into the third position; and a detent release element that is movable into an unlock position, wherein the detent release element in the unlock position is configured for acting on the follower to move the follower from the deployment stop position into a deployment release position, thereby freeing the deployment control element for movement from the second position to the third position.

The follower may be movable into the deployment stop position from a detent stop position in which the follower blocks movement of the detent release element into the unlock position in one embodiment. In that case, the detent release element may be substantially immovable from a lock position into the unlock position until enabled by movement of the follower into the deployment stop position. The detent release element may be substantially immovable from a lock position into the unlock position until enabled by movement of the follower from the detent stop position to the deployment stop position.

The follower may be in the detent stop position when the deployment control element is in the first position, and may be biased toward the detent stop position. More generally, the follower may be movable against bias into the deployment stop position and the deployment release position.

The deployment control element could be movable between the first, second and third positions along a trigger axis, the follower could be movable between a detent stop (e.g., detent stop position) and detent release positions (e.g., a deployment release position) along a follower axis that is transverse to the trigger axis, and the detent release element could be movable between the lock and unlock positions along a detent axis. The detent axis may be substantially parallel to the trigger axis.

A trigger ramp movable with the deployment control element may be opposed to the follower and may be inclined relative to the trigger axis such that movement of the deployment control element along the trigger axis toward the second position causes the ramp formation to slide relative to the follower to drive movement of the follower along the follower axis into the detent release position. The trigger ramp can be shaped to engage the follower when the deployment control element reaches the second position, thereby blocking further movement of the deployment control element toward the third position. The trigger ramp may, for example, comprise a shoulder that extends transversely relative to an inclined surface of the trigger ramp and that is opposed to the follower. The deployment control element may include grip formations arranged to facilitate gripping and pulling the deployment control element outwardly from the second position to the first position.

In several embodiments, a deployment system for deploying an implant in a patient's body comprises a deployment drive that is configured to operate in response to movement of a deployment control element from a first position in which the implant is undeployed, to a second position in which the implant is partially deployed, and to a third position in which the implant is fully deployed; and a detent mechanism that is configured to block movement of the deployment control element from the second position to the third position, wherein the detent mechanism comprises: a follower that is configured to move into a deployment stop position, thereby blocking movement of the deployment control element into the third position; and a detent release element configured to move the follower from the deployment stop position into a deployment release position, the deployment release position being configured to free the deployment control element for movement from the second position to the third position.

The follower may comprise a barrier member that is in blocking opposition to a formation of the detent release element when the follower is in the detent stop position and an opening that is in receiving opposition to that formation when the follower is in the detent release position. For example, the barrier member and the opening may be disposed in succession along the follower axis.

The formation of the detent release element could comprise a detent ramp that is opposed to the follower and that is inclined relative to the detent axis, such that movement of the detent release element along the detent axis toward the unlock position causes the detent ramp to slide relative to the follower to drive movement of the follower along the follower axis beyond the enabling position into a release position that frees the deployment control element for movement from the second position into the third position. That movement of the follower into the release position suitably disengages the follower from the trigger ramp, for example by lifting the follower clear of the shoulder.

The deployment control element may comprise grip formations that are arranged to facilitate gripping and pulling the deployment control element outwardly from the second position to the first position.

Several embodiments of the invention can also be expressed as a method of operating an implant-deployment device, the method comprising: moving a deployment control element of the device from a first position in which an implant is undeployed, to a second position in which the implant is partially deployed; by said movement of the deployment control element acting on a follower of the device, moving the follower into a deployment stop position that blocks further movement of the deployment control element into a third position in which the implant is fully deployed; and moving a detent release element of the device into an unlock position, said movement of the detent release element acting on the follower to move the follower into a deployment release position that frees the deployment control element for movement from the second position to the third position.

In one embodiment, a method of operating an implant-deployment device (e.g., for optionally treating benign prostatic hyperplasia) may include: moving a deployment control element of the device from a first position in which an implant is undeployed, to a second position in which the implant is partially deployed in a urethra; wherein moving the deployment control element from the first position to the second position acts on a follower of the device, thereby moving the follower into a deployment stop position that blocks further movement of the deployment control element into a third position in which the implant is fully deployed in the urethra; and moving a detent release element of the device into an unlock position, wherein moving the detent release element acts on the follower, thereby moving the follower into a deployment release position that frees the deployment control element for movement from the second position to the third position.

The follower can be moved into the deployment stop position from a detent stop position in which the follower blocks movement of the detent release element into the unlock position.

The deployment control element and the detent release element suitably act on the follower with respective cam actions. The deployment control element and the detent release element may be movable along substantially parallel axes.

The follower could be moved in a direction transverse to directions of movement of the deployment control element and the detent release element. The follower can be biased against the deployment control element and the detent release element. Similarly, the follower can be moved against bias into the deployment stop position and the deployment release position.

In several embodiments, the method comprises an implant-deployment device that further comprises a housing and an elongate delivery tube. The elongate delivery tube may include an inner element comprising an imaging head, an intermediate element comprising implant retainer formations, and an outer element comprising an outer sheath that is co-operable with the implant retainer formations. In one embodiment, the inner element, the intermediate element, and the outer element are arranged in radially outward succession. In several embodiments, moving the deployment control element from the first position to the second position comprises retracting the outer element and the inner elements relative to the intermediate element. In one embodiment, moving the detent release element to the unlock position comprises retracting the outer element relative to the intermediate element and the inner elements, wherein the outer sheath is retracted proximally beyond the implant retainer formations to release the implant.

In several embodiments, a method of operating an implant-deployment device (e.g., for treating benign prostatic hyperplasia) comprises: moving a deployment control element of the device from a first position to a second position, wherein an implant is undeployed in the first position, wherein the implant is partially deployed in the second position; wherein moving the deployment control element from the first position to the second position moves a follower to a deployment stop position that blocks movement of the deployment control element out of the second position; and moving a detent release element of the device, thereby moving the follower into a deployment release position that frees the deployment control element for movement from the second position to a third position in which the implant is fully deployed in a urethra.

The method may comprise moving the follower into the deployment stop position from a detent stop position in which the follower blocks movement of the detent release element into the unlock position. The method may include having the deployment control element and the detent release element act on the follower with respective cam actions. The method, according to several embodiments, may also include one or more of the following: moving the deployment control element and the detent release element along substantially parallel axes; moving the follower in a direction transverse to directions of movement of the deployment control element and the detent release element; biasing the follower against the deployment control element and the detent release element; and/or moving the follower against bias into the deployment stop position and into the deployment release position.

In one embodiment, the implant-deployment device further comprises a housing and an elongate delivery tube. The elongate delivery tube may comprise an inner element comprising an imaging head, an intermediate element comprising implant retainer formations, and an outer element comprising an outer sheath that is co-operable with the implant retainer formations.

In one embodiment, the inner element, the intermediate element, and the outer element are arranged in radially outward succession, wherein the moving the deployment control element from the first position to the second position comprises retracting the outer element and the inner elements relative to the intermediate element, wherein the moving the detent release element to the unlock position comprises retracting the outer element relative to the intermediate element and the inner elements, and wherein the outer sheath is retracted proximally beyond the implant retainer formations to release the implant.

In several embodiments, a method of operating an implant-deployment device comprises providing a device comprising: a housing; an elongate delivery tube comprising delivery tube elements extending from the housing, the delivery tube elements comprising, in radially outward succession: an inner element comprising an imaging head, an intermediate element comprising two or more implant retainer formations, and an outer element comprising an outer sheath; wherein the device is provided in an undeployed state, thereby retaining an implant engaged with the two or more implant retainer formations; retracting the outer and inner elements relative to the intermediate element by moving a hub carriage into a partially deployed state relative to an intermediate element hub held in fixed relation to the housing, the hub carriage carrying an outer element hub and an inner element hub; releasing a detent mechanism blocking a movement of the hub carriage from a partially deployed state to a deployed state; and moving the hub carriage into a deployed state, further retracting the outer element relative to the intermediate and inner elements to release the implant.

The inner element hub may be latched relative to the hub carriage during movement of the hub carriage between the undeployed state and the partially deployed state. Movement of the inner element hub relative to the housing may be blocked during movement of the hub carriage between the partially deployed state and the deployed state for treatment of benign prostatic hyperplasia. The hub carriage may be releasably latched relative to the housing when in the undeployed state. A deployment control element may be operated to drive longitudinal movement of the hub carriage. Operating the deployment control element may cause a deployment drive of the implant-deployment device to move the hub carriage from the undeployed state to the partially deployed state. A detent mechanism of the deployment drive may block the moving of the hub carriage from the partially deployed state to the deployed state.

In several embodiments, a device for deploying an implant in a patient's body comprises: an elongate delivery tube having delivery tube elements in concentric relation, those delivery tube elements being, in radially outward succession, an inner element comprising an imaging head, an intermediate element comprising implant retainer formations and an outer element comprising an outer sheath that is co-operable with the implant retainer formations, the inner and outer elements being retractable relative to the intermediate element along a longitudinal axis of the delivery tube; and a handle at a proximal end of the delivery tube, the handle having a housing that contains: a hub assembly comprising an inner element hub, an intermediate element hub and an outer element hub, each of those hubs being mounted proximally to a respective one of the delivery tube elements; a hub carriage that is movable longitudinally with respect to the housing and to the intermediate element hub and that supports the inner element hub and the outer element hub for said movement with the hub carriage to retract the inner and outer elements relative to the intermediate element of the delivery tube; and a deployment drive that is configured to drive said movement of the hub carriage in response to operation of a deployment control element that is external to the housing. In several embodiments, a hub carriage is a hub casing.

In several embodiments, a device for deploying an implant in a patient's body comprises an elongate delivery tube having delivery tube elements in concentric relation, the delivery tube elements comprising, in radially outward succession: an inner element comprising an imaging head, an intermediate element comprising implant retainer formations, and an outer element comprising an outer sheath that is co-operable with the implant retainer formations, the inner and outer elements being retractable relative to the intermediate element along a longitudinal axis of the delivery tube; and a handle at a proximal end of the delivery tube. The handle may have a housing that comprises: a hub assembly comprising an inner element hub, an intermediate element hub and an outer element hub, wherein the inner element hub is mounted proximally to the inner element of the delivery tube, wherein the intermediate element hub is mounted proximally to the intermediate element of the delivery tube, wherein the outer element hub is mounted proximally to the outer element of the delivery tube; a hub carriage configured for longitudinal movement with respect to the housing and to the intermediate element hub and that supports the inner element hub and the outer element hub for the longitudinal movement with the hub carriage to retract the inner and outer elements relative to the intermediate element of the delivery tube; and a deployment drive that is configured to drive the longitudinal movement of the hub carriage in response to operation of a deployment control element that is external to the housing.

In some embodiments, the hub carriage may be movable proximally by the deployment drive relative to the housing and the intermediate element hub along a longitudinally-extending retraction path from an undeployed position in which the outer sheath is opposed to and in a distally advanced position relative to the implant retainer formations to a deployed position in which the outer sheath is retracted proximally beyond the implant retainer formations, via an intermediate partially deployed position in which the outer element is retracted proximally from the distally advanced position while still being opposed to the implant retainer formations.

The outer element hub and the inner element hub may be movable proximally with the hub carriage from the undeployed position to the partially deployed position. In that case, the outer element hub and the inner element hub may be reversible with the hub carriage in a distal direction along the retraction path from the partially deployed position to the undeployed position.

The outer element hub may be movable proximally with the hub carriage relative to the inner element hub as the hub carriage moves from the partially deployed position to the deployed position. In that case, the outer element hub may be fixed relative to the hub carriage and the inner element hub may be releasably latched relative to the hub carriage. For example, a stop formation in fixed relation to the housing may be positioned in the retraction path proximally of the inner element hub to block proximal movement of the inner element hub beyond the partially deployed position of the hub carriage. This causes the inner element hub to unlatch from the hub carriage while allowing continued proximal movement of the hub carriage and the outer element hub from the partially deployed position to the deployed position.

The hub carriage may be releasably latched relative to the housing when in the undeployed position, that latching being releasable by operation of the deployment control element. In one embodiment, the hub carriage is releasably latched relative to the housing when in the undeployed position, wherein the hub carriage is configured to be releasable by operation of the deployment control element.

The deployment drive preferably comprises a detent mechanism that is configured to block movement of the hub carriage from the partially deployed position to the deployed position and a detent release element that is operable to release the detent mechanism to allow the hub carriage to move from the partially deployed position to the deployed position. For example, the detent release element may be enabled to release the detent mechanism by virtue of movement of the deployment control element that acts on the deployment drive to move the hub carriage from the undeployed position to the partially deployed position. In this respect, the deployment control element could block movement of the detent release element when the hub carriage is in the undeployed position.

In several embodiments, a device configured for deploying an implant in a patient's body comprises a delivery tube comprising: an inner element comprising an imaging head, an intermediate element comprising two or more implant retainer formations, and an outer element comprising an outer sheath, wherein the inner element, intermediate element, and outer element are arranged in concentric relation, wherein the inner and outer elements are movable relative to the intermediate element along a longitudinal axis of the delivery tube; and a handle. The handle may include a housing, a hub assembly comprising an inner element hub, an intermediate element hub and an outer element hub, wherein the inner element hub is mounted proximally to the inner element of the delivery tube, wherein the intermediate element hub is mounted proximally to the intermediate element of the delivery tube, wherein the outer element hub is mounted proximally to the outer element of the delivery tube; a hub carriage configured for longitudinal movement with respect to the housing and that supports the inner element hub and the outer element hub for the longitudinal movement with the hub carriage to move the inner and outer elements relative to the intermediate element of the delivery tube; and a deployment drive configured to drive the longitudinal movement of the hub carriage in response to operation of a deployment control system.

The outer element hub, the intermediate element hub and the inner element hub can be disposed in proximal succession along the hub carriage. The hub carriage may comprise a distal portion that supports the outer element hub, a proximal portion that supports the inner element hub, and a longitudinally-extending intermediate portion that connects the distal and proximal portions and bridges around the intermediate element hub. The intermediate element hub may suitably be sandwiched between the outer element hub and the inner element hub and could be at least partially housed within the hub carriage.

The intermediate element hub may have at least one support that extends laterally beyond the hub carriage to fix the intermediate element hub against movement relative to the housing. In that case, a side wall of the hub carriage could comprise a longitudinally-extending slot that accommodates the laterally-extending support of the intermediate element hub to allow for movement of the hub carriage relative to the intermediate element hub. Such a slot suitably has an open proximal end.

The deployment drive may comprise a gearset that acts between the deployment control element and the hub carriage. In that case, the hub carriage may have a longitudinally-extending rack formation that is engaged with a gear of the deployment drive gearset. For example, the rack formation could be on an arm that extends proximally from the hub carriage. The arm may be offset laterally from a central longitudinal axis that extends proximally into the housing from the delivery tube, in which case the rack formation could face that axis.

In one embodiment, the inventive concept embraces a corresponding method of operating an implant-deployment device having elongate delivery tube elements in concentric relation extending from a housing, those elements being, in radially outward succession, an inner element comprising an imaging head, an intermediate element comprising implant retainer formations and an outer element comprising an outer sheath that is co-operable with the implant retainer formations. In several embodiments, the method comprises: providing the device in an undeployed state in which the outer sheath is opposed to and in a distally advanced position relative to the implant retainer formations, thereby retaining an implant engaged with those formations; retracting the outer and inner elements relative to the intermediate element into a partially deployed state by moving a hub carriage of the device relative to a hub of the intermediate element held in fixed relation to the housing, the hub carriage carrying a hub of the outer element and a hub of the inner element; and moving the hub carriage, carrying the hub of the outer element, with respect to the hub of the intermediate element, hence further retracting the outer element relative to the intermediate element into a deployed state in which the outer sheath is retracted proximally beyond the implant retainer formations to release the implant.

In several embodiments, a method of operating an implant-deployment device comprises providing an implant-deployment device in an undeployed state, the implant-deployment device comprising: an elongate delivery tube comprising elongate delivery tube elements in concentric relation and extending from a housing, the delivery tube elements comprising, in radially outward succession: an inner element comprising an imaging head, an intermediate element comprising implant retainer formations, and an outer element comprising an outer sheath that is co-operable with the implant retainer formations. The undeployed state may comprise the outer sheath being opposed to and in a distally advanced position relative to the implant retainer formations, thereby retaining an implant engaged with the implant retainer formations. The method may include retracting the outer element and the inner element relative to the intermediate element into a partially deployed state by moving a hub carriage of the implant-deployment device relative to an intermediate element hub held in fixed relation to the housing, the hub carriage carrying an outer element hub and an inner element hub; and moving the hub carriage, carrying the outer element hub, with respect to the intermediate element hub and inner element hub, thereby retracting the outer element relative to the intermediate element and the inner element into a deployed state, wherein the deployed states comprises the outer sheath being retracted proximally beyond the implant retainer formations to release the implant (e.g., in a urethra).

In several embodiments, the method comprises moving the outer element hub and the inner element hub proximally with the hub carriage to move the hub carriage into the partially deployed state. The method may include moving the outer element hub proximally with the hub carriage relative to the inner element hub to move the hub carriage into a deployed state, wherein the deployed state is configured for releasing the implant in the urethra.

In some embodiments, the hub carriage may be releasably latched relative to the housing when in the undeployed state. Similarly, the hub of the inner element may be latched relative to the hub carriage during movement of the hub carriage between the undeployed and partially deployed states. Movement of the hub of the inner element relative to the housing may be blocked during movement of the hub carriage between the partially deployed and deployed states, thereby unlatching the hub of the inner element from the hub carriage.

In some embodiments, moving the hub carriage into the partially deployed state also moves the outer element hub and inner element hub proximally with the hub carriage. Movement of the hub carriage into a deployed state may also move the outer element proximally with the hub carriage relative to the inner element hub. The operation of a deployment control element may release the hub carriage from its latching to the housing. In such an embodiment, the operation of the deployment control element may cause a deployment drive of the device to drive the movement of the hub carriage from the undeployed state to the partially deployed state. In several embodiments, a detent mechanism of the deployment drive blocks the movement of the hub carriage from the partially deployed position to the deployed position. In such an embodiment, the operation of a deployment control element may enable a detent release element to release the detent mechanism. For example, depressing the detent release element may release the detent mechanism, allowing for the movement of the hub carriage from the partially deployed position to the deployed position. In one embodiment, operation of the deployment control element may engage a gearset of the deployment drive, and the gearset may engage with an extending rack formation of the hub carriage for controlling movement of the hub carriage. The operation of a deployment control element may allow for both movement of the hub carriage from the undeployed state to the partially deployed state, or movement of the hub carriage from the partially deployed state to the undeployed state.

In several embodiments, the method may include moving the outer element hub and the inner element hub proximally with the hub carriage to move the hub carriage into the partially deployed state. The method may include moving the outer element hub proximally with the hub carriage relative to the inner element hub to move the hub carriage into a deployed state. The method may include latching the inner element hub relative to the hub carriage during movement of the hub carriage between the undeployed state and the partially deployed state. The method may include blocking movement of the inner element hub relative to the housing during movement of the hub carriage between the partially deployed and deployed states. The method may include releasably latching the hub carriage relative to the housing when in the undeployed state. The method may include operating a deployment control element to drive longitudinal movement of the hub carriage. The method may include operating the deployment control element to cause a deployment drive of the implant-deployment device to move the hub carriage from the undeployed state to the partially deployed state. The method may include use of a detent mechanism of the deployment drive to block the moving of the hub carriage from the partially deployed position to the deployed position. The deployment control element may move a detent release element thereby releasing the detent mechanism. The method may include depressing the detent release element to release the detent mechanism, allowing for the moving of the hub carriage from the partially deployed position to the deployed position. The method may include operating the deployment control element to engage a gearset of the deployment drive, the gearset engaging with an extending rack formation of the hub carriage for controlling movement of the hub carriage. The method may include operating the deployment control element to allow for moving of the hub carriage from the undeployed state to the partially deployed state, and/or moving of the hub carriage from the partially deployed state to the undeployed state.

According to several embodiments, the inventive concept can also be expressed in terms of an implant delivery device that comprises: an elongate flexible implant delivery element; a housing from which the delivery element extends; a steering system within the housing and acting on the delivery element to bend the delivery element along its length under user control of a steering lever that is pivotable relative to the housing about a pivot axis disposed within the housing; and mutually engageable locking formations within the housing, comprising a first locking formation that is pivotable with the steering lever and a second locking formation that is fixed relative to the housing. The steering lever is movable toward the pivot axis from a locked position, in which inter-engagement of the locking formations locks the steering lever against said pivotal movement, into an unlocked position in which disengagement of the locking formations frees the steering lever for said pivotal movement. The steering lever may be biased away from the pivot axis toward the locked position.

The second locking formation may, for example, be formed integrally with the housing on an inner face of the housing. The second locking formation can be curved about the pivot axis, in which case a centre of curvature of the second locking formation may be coincident with the pivot axis.

The steering lever may be movable toward and away from the pivot axis on a locking axis that intersects the second locking formation. The second locking formation may be disposed between the pivot axis and an outer end of the steering lever.

Steering wires can extend into the delivery element from a steering dial that is pivotable with the steering lever. In that case, the steering lever may be movable relative to a hub of the steering dial along an axis intersecting the pivot axis, but may be fixed against movement relative to the hub about the pivot axis.

BRIEF DESCRIPTION OF THE DRAWINGS

In order that various embodiments of the invention may be more readily understood, reference will now be made, by way of example, to the accompanying drawings in which.

The figures are non-limiting and represent some embodiments of the invention. Elements of different figures may be combined with each other.

DETAILED DESCRIPTION

Figure 1:
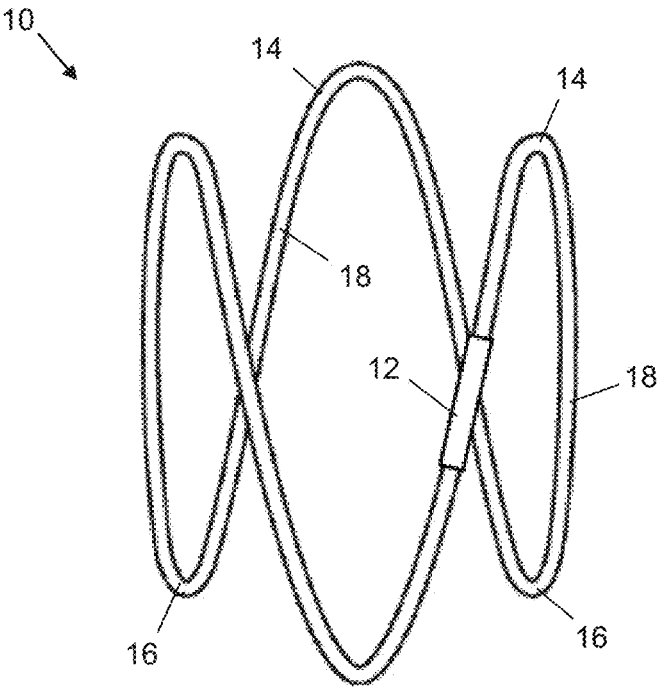
FIG. 1 is a side view of an expander in an expanded state suitable for use with embodiments of the invention.

To place several embodiments of the invention in context, reference is made firstly to FIG. 1 which shows an expandable implant or expander 10 suitable for use with embodiments of the present invention. The expander 10 shown in FIG. 1 is an example only: the delivery device to be described herein may be suitable for use, or may be adapted for use, with other implants.

In some embodiments, expander 10 comprises a single nitinol wire whose opposed ends are joined by a sleeve 12 to form a continuous sinusoidally-undulating ring. When released, the expander 10 can self-expand by elastic recovery from a radially-compressed state for stowage into a radially-expanded state for deployment as shown in FIG. 1. Specifically, the nitinol wire ring of the expander 10 can act with superelastic shape memory properties such that when in a compressed state, the expander 10 may be configured to exert an outward radial force on a surrounding body structure into which it is deployed, in particular the prostatic urethra.

In one embodiment, the expander 10 has a proximal end comprising three proximal prongs with respective proximal apices 14 and a distal end comprising three distal prongs with respective distal apices 16. The proximal and distal apices 14, 16 may be joined, in circumferential alternation, by longitudinal struts 18. Each strut 18 can have an outwardly convex shape that lends a barrel-like profile to the expander 10 when viewed in outline.

When in a radially-compressed state, the expander 10 may be narrowed to the extent that it can be advanced along the penile urethra of a patient with minimal discomfort. The expander 10 may be delivered to the prostatic urethra in that contracted state and is then released to self-expand in situ.

Figure 2:
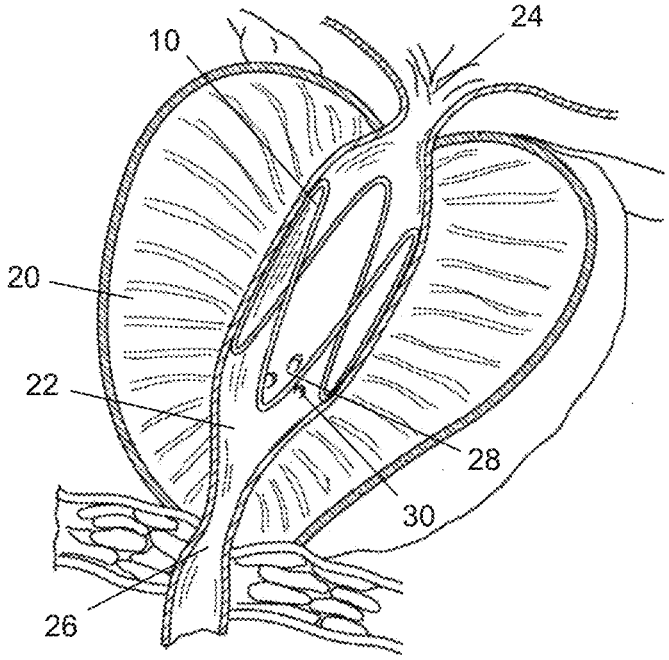
FIG. 2 is a cut-away view of a prostate of a patient with the expander of FIG. 1 disposed within the prostatic urethra to treat BPH by exerting an outward radial pressure on the walls of the prostatic urethra, hence effecting dilation.

Referring now also to FIG. 2, the expander 10 is shown in use within the prostate gland 20 to treat symptoms of benign prostatic hyperplasia (BPH) according to one embodiment. Specifically, the expander 10 is located in the prostatic urethra 22 within the prostate 20 between the bladder neck 24 and the external sphincter 26. When located in that longitudinal position, the expander 10 exerts an outward radial force against the lobes of the prostatic urethra 22 to ease the passage of urine flowing from the bladder.

In various embodiments, care may be taken to ensure that the expander 10 is at the correct longitudinal position between the bladder neck 24 and the external sphincter 26 before deployment. In this respect, positioning the expander 10 too close to either the bladder neck 24 or the external sphincter 26 can be undesirable as their muscle action could otherwise cause the expander 10 to migrate along the urethra or into the bladder over time.

In several embodiments, the expander 10 may also be orientated angularly such that the verumontanum 28 and the seminal ducts 30 are unobstructed by the undulating wire of the expander 10, thus preserving the patient's sexual function. Furthermore, the longitudinal struts 18 of the expander 10 are oriented to engage respective lobes of the prostate 20, thereby exerting an outward radial force on each lobe to maintain an open passage between the bladder neck 24 and the external sphincter 26.

Figure 3:
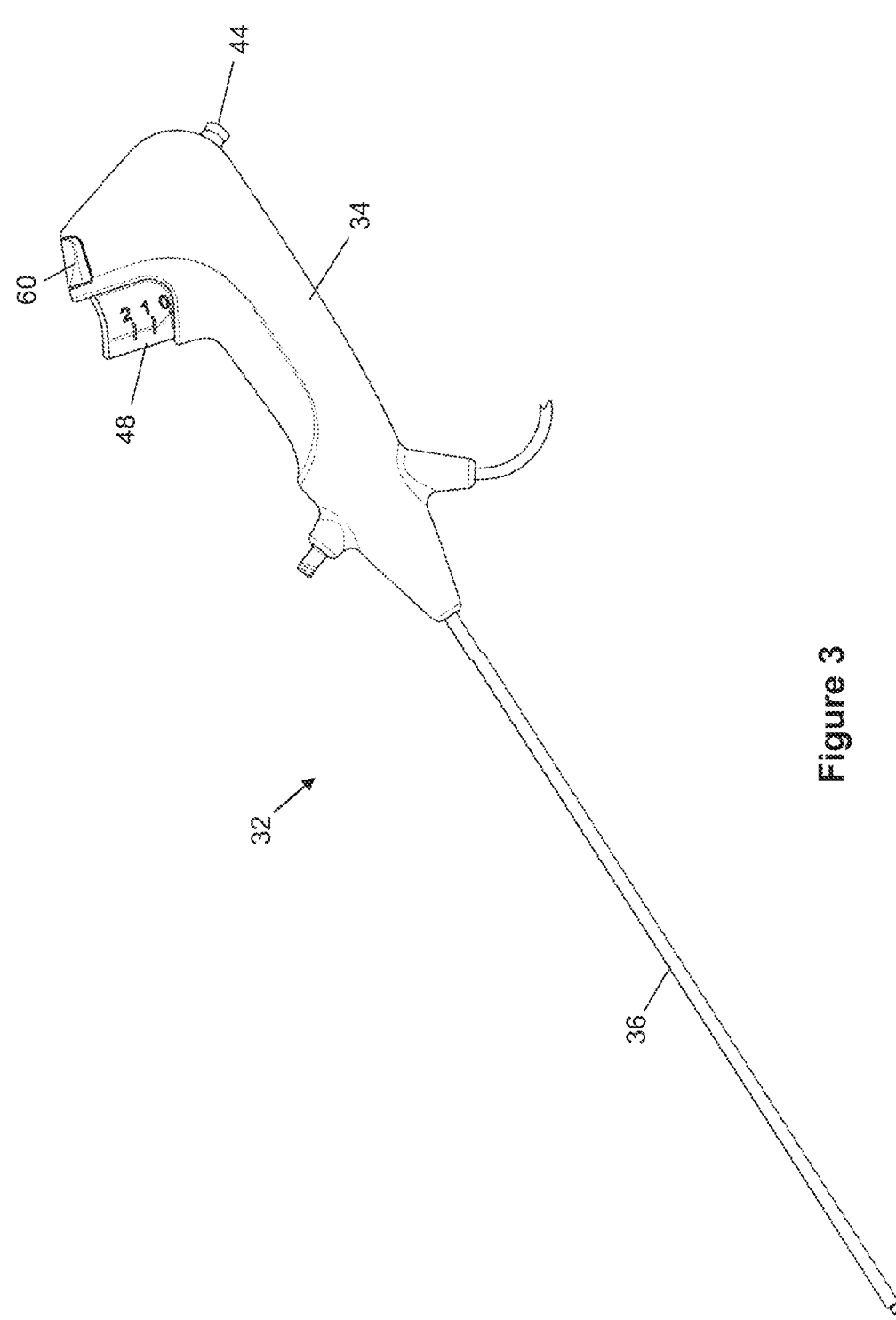
FIG. 3 is a side view of a delivery device of the invention comprising a handle and a delivery tube.
Figure 4:
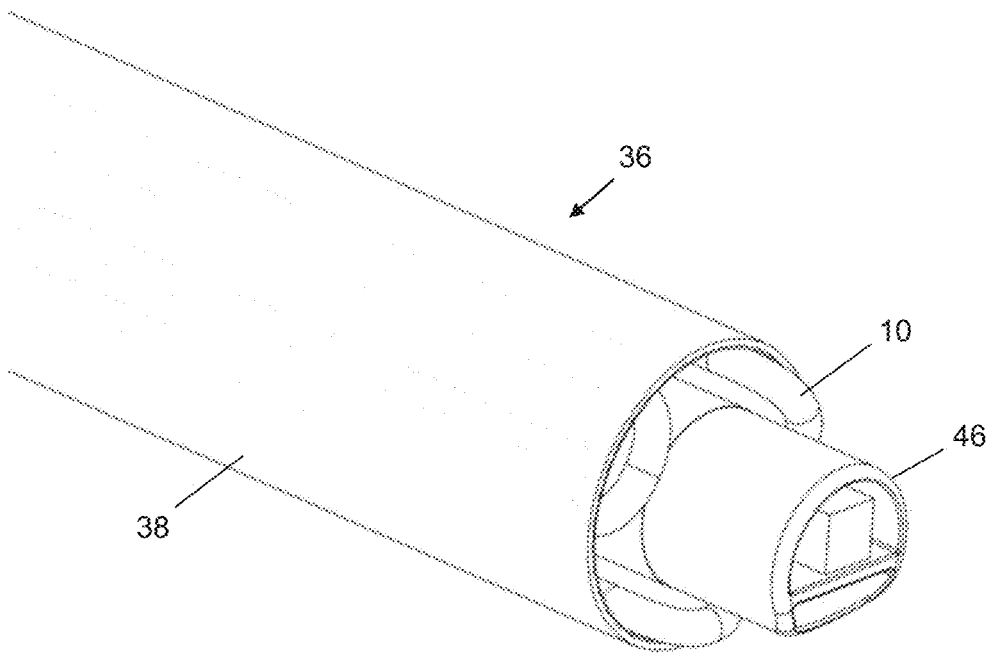
FIG. 4 is an enlarged detail perspective view of a distal end portion of the delivery tube containing an undeployed expander, when the device is in a deployment stage zero.

Moving on now to FIG. 3, an embodiment of a device 32 for deploying a self-expanding implant or expander 10 comprises a proximal handle 34 acting on a flexible delivery tube 36 that extends distally from the handle 34. Initially, as shown in FIGS. 4 and 8*a*, the expander 10 is sheathed within a distal end portion of the delivery tube 36 in a radially compressed state, ready for insertion and delivery to a target deployment site in the prostatic urethra.

Figures 8A, 8B, 8C:
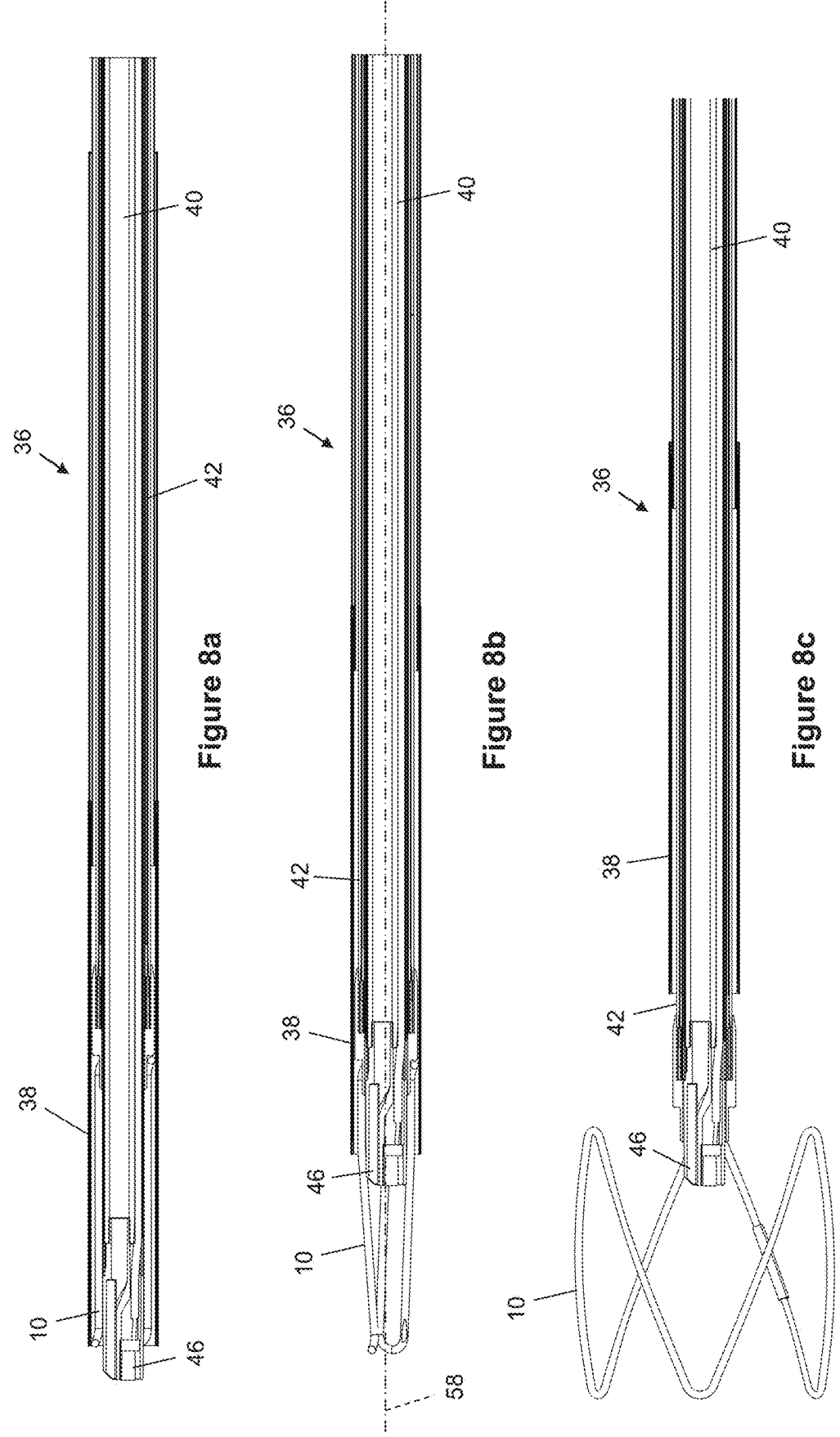
FIGS. 8a, 8b and 8c are sectional side views of the distal end portion of the delivery tube corresponding, respectively, to the deployment stages of the device shown in FIGS. 4, 5 and 7.

As will be explained, and as shown in FIGS. 8*a*, 8*b* and 8*c*, an embodiment of the delivery tube 36 comprises three flexible tubular elements in concentric longitudinally-sliding relation, namely: an outer element 38 comprising an outer sheath; an inner element 40 comprising an imaging sheath; and an intermediate element 42 comprising a steering sheath disposed in an annular gap defined between the outer sheath and the imaging sheath.

A user operating the device 32 can operate a steering lever 44 on the handle 34 to steer the delivery tube 36 during navigation along the urethra to the target site. Operation of the steering lever 44 acts on the intermediate element 42 to deflect the distal end portion of the delivery tube 36 relative to a proximal portion of the delivery tube 36.

In several embodiments, the inner element 40 of the delivery tube 36 has an imaging system (e.g., an imaging head) at its distal end that provides the user with images of the urethra, taken from a viewpoint on a longitudinal axis that is radially inboard of the expander 10 in the distal end portion of the delivery tube 36. In this example, as shown in FIGS. 4 and 8*a*, a camera tip 46 (or other imaging or sensing technology) defining the distal extremity of the inner element 40, with image-capturing and lighting components adjacent an irrigation duct, initially protrudes distally from the distal end of the outer element 38. This ensures the best possible field of view as the delivery tube 36 navigates the anatomy before deployment of the expander 10. However, in other examples, the distal extremity of the inner element 40 could be substantially level with the distal end of the outer element 38 or could even be recessed proximally to a small extent, provided that an adequate field of view is maintained.

Before reaching the deployment site, the expander 10 can remain sheathed by the outer element 38 within the distal end portion of the delivery tube 36 as shown in FIGS. 4 and 8*a*. As deployment of the expander 10 has therefore not yet begun, this stage or initial undeployed state will be referred to in the following description as 'deployment stage zero'.

Figure 5:
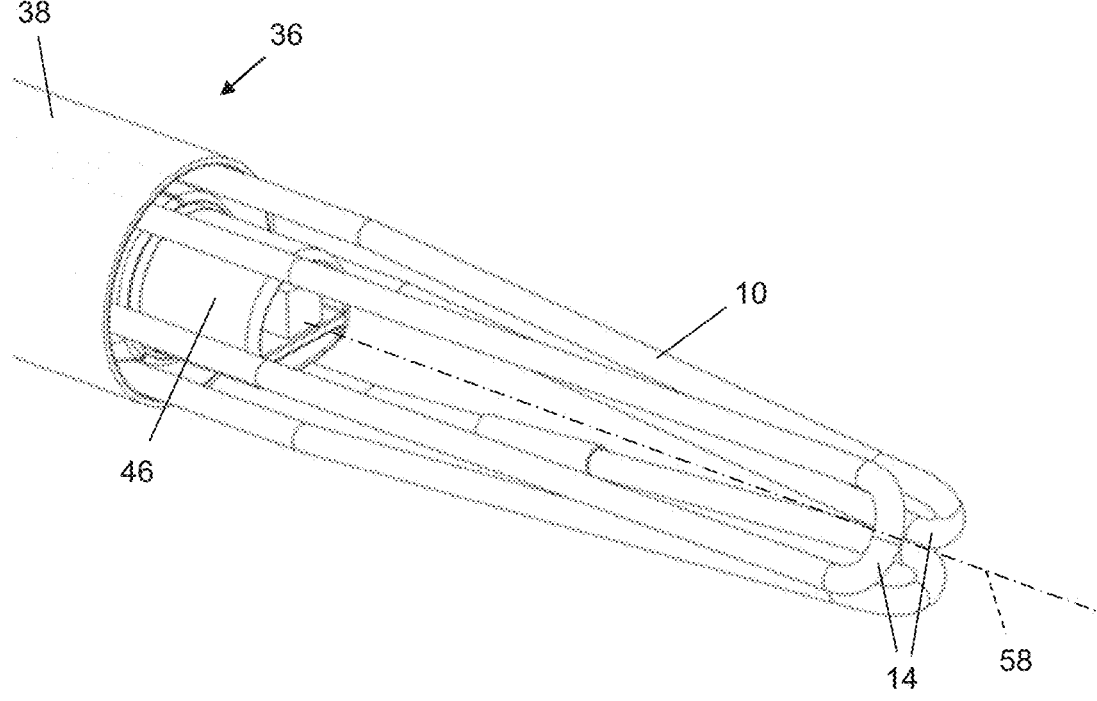
FIG. 5 corresponds to FIG. 4 but shows the device in a deployment stage one with the expander partially deployed.

In one embodiment, when the expander 10 is at or near to the deployment site, the user operates a deployment control element, namely a trigger 48 external to the handle 34, which acts on the delivery tube 36 to unsheath the expander 10 partially as shown in FIGS. 5 and 8b. This stage or intermediate state will be referred to in the following description as 'deployment stage one'. The imaging system of the camera tip 46 can then provide images of the distal end of the expander 10 against the surrounding structures of the prostatic urethra.

When in deployment stage one, the action of the deployment trigger 48 is reversible to return the device 32 to deployment stage zero. Thus, the expander 10 can be re-sheathed if the user decides to re-position the expander 10 substantially or to abandon the procedure.

FIG. 8b shows how, in the partially-deployed configuration of deployment stage one, the outer element 38 and the inner element 40, including the camera tip 46, are pulled back proximally relative to the intermediate element 42 and hence also relative to the expander 10 supported by the intermediate element 42. Thus, beneficially, the imaging device of the camera tip 46 when in the retracted position can visualise the expander 10 against a backdrop of the adjacent anatomy, from a viewpoint within the expander 10. The retracted outer element 38 remains out of the field of view of the imaging device.

The prongs terminating in the distal apices 14 of the expander 10 can contact the lobes of the prostate 20 so that a user may view and fully appreciate the position of the expander 10 relative to the structures around the prostatic urethra 22 before full deployment. Advantageously, this enables the user to check if the expander 10 is positioned correctly prior to full deployment.

Figure 6:
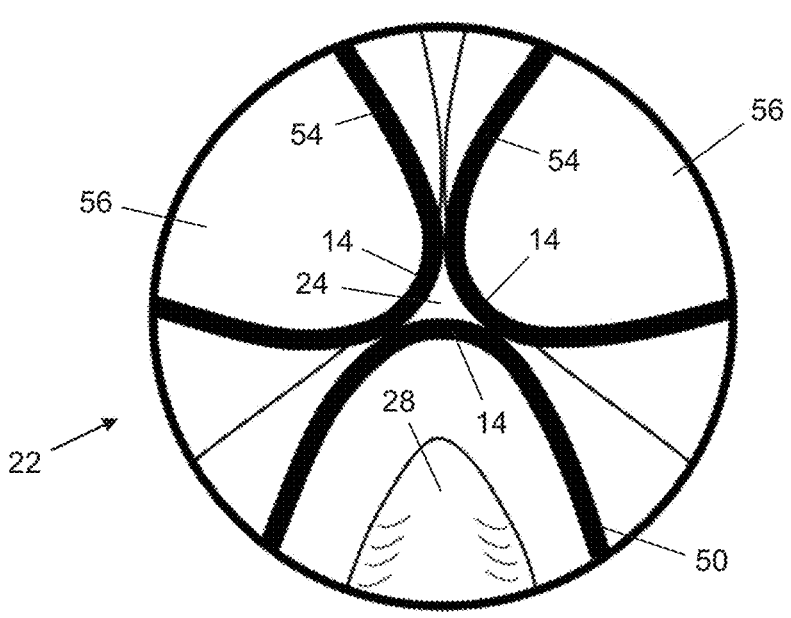
FIG. 6 is a schematic view of an image captured by an imaging chip of the device when the device is in deployment stage one as shown in FIG. 5, in use.

To illustrate this, FIG. 6 is a schematic view of an image captured by an imaging device of the camera tip 46 when the outer element 38 is in the partially-deployed position. This shows the distal apices 14 of the expander 10 aligned with and contacting the lateral prostatic lobes around the prostatic urethra 22. Specifically, a posterior prong 50 of the expander 10 is shown surrounding or straddling the verumontanum 28 whereas the two anterior prongs 54 of the expander 10 are oriented such that they engage the anterior lateral lobes 56.

It will be apparent that the image provided to the user by the imaging device of the camera tip 46 beneficially allows simultaneous visualisation of the longitudinal position of the expander 10 relative to the anatomy, for example the verumontanum 28 and the bladder neck 24, and also the angular position of the expander 10 relative to the verumontanum 28 and the prostatic lobes 56. This facilitates accurate positioning of the expander 10 within the prostatic urethra 22.

It will also be noted from FIGS. 5, 6 and 8b that the aforementioned barrelled outline of the expander 10 causes the distal apices 14 of the expander 10 to converge toward a central longitudinal axis 58 when the camera tip 46 of the inner element 40 is retracted within the expander 10. This brings the distal apices 14 into, or close to, mutual contact and so places them in a prominent central position in the user's field of view, hence serving as an effective aiming point to guide the user.

Figure 7:
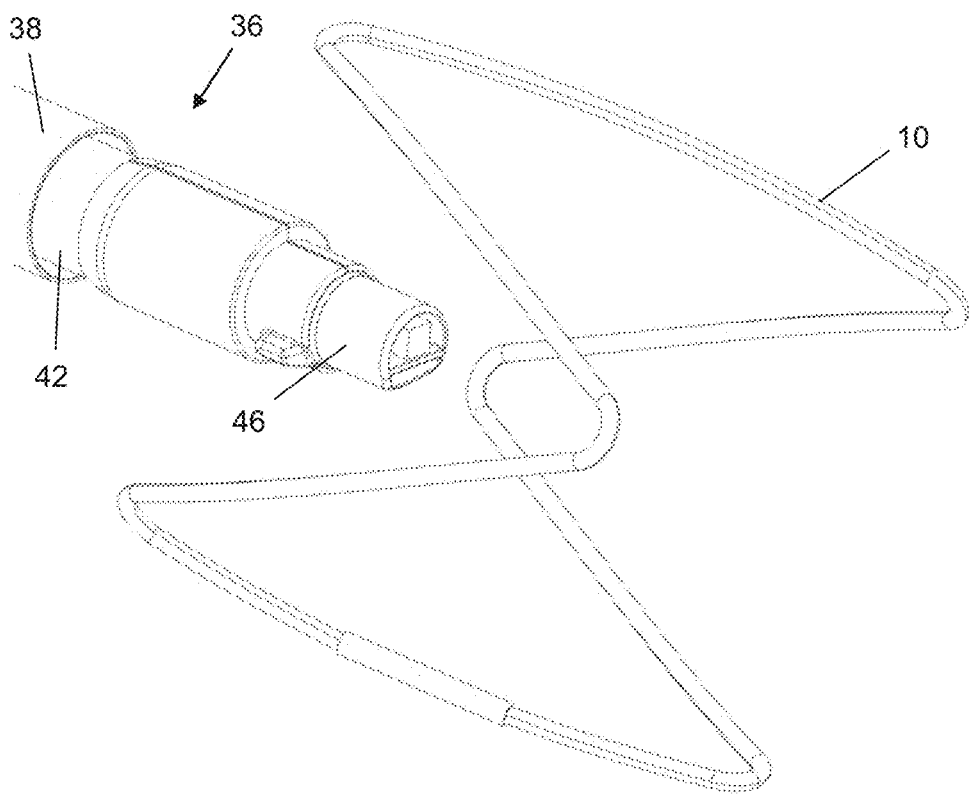
FIG. 7 corresponds to FIGS. 4 and 5 but shows the device in a deployment stage two with the expander fully deployed.

In one embodiment, when satisfied that the expander 10 is correctly positioned at the deployment site, the user can operate the deployment trigger 48 to unsheath the expander 10 fully for deployment as shown in FIGS. 7 and 8c. This stage or final deployed state will be referred to in the following description as 'deployment stage two'. Once fully unsheathed by retracting the outer element 38, the expander 10 expands radially at the target site and is thereby released from the delivery tube 36 into a deployed state within the prostatic urethra 20. In the example of the invention to be described, the inner element 40 does not retract further with the outer element 38 so that the viewpoint of the camera tip 46 remains fixed from deployment stage one to deployment stage two.

A detent mechanism prevents inadvertent deployment of the expander 10 by blocking operation of the deployment trigger 48 that could otherwise unsheath the expander 10 fully. Specifically, at deployment stage one, the user must deliberately depress a detent release element, such as a detent button 60, before the deployment trigger 48 can be operated to unsheath and deploy the expander 10 in deployment stage two.

The detent button 60 is rendered inoperable when the device 32 is at deployment stage zero. Movement of the deployment trigger 48 to bring the device 32 to deployment stage one enables operation of the detent button 60. The detent button 60 can then be operated by a separate and deliberate movement of a user's finger to release the deployment trigger 48 for further movement to bring the device 32 to deployment stage two.

During partial and full unsheathing, the axial and angular position of the expander 10 remains fixed relative to the handle 34, steering aside, so as to maintain accurate positioning of the expander 10 at the deployment location. The angular position of the expander 10 also remains fixed relative to the imaging device of the camera tip 46.

Figure 9:
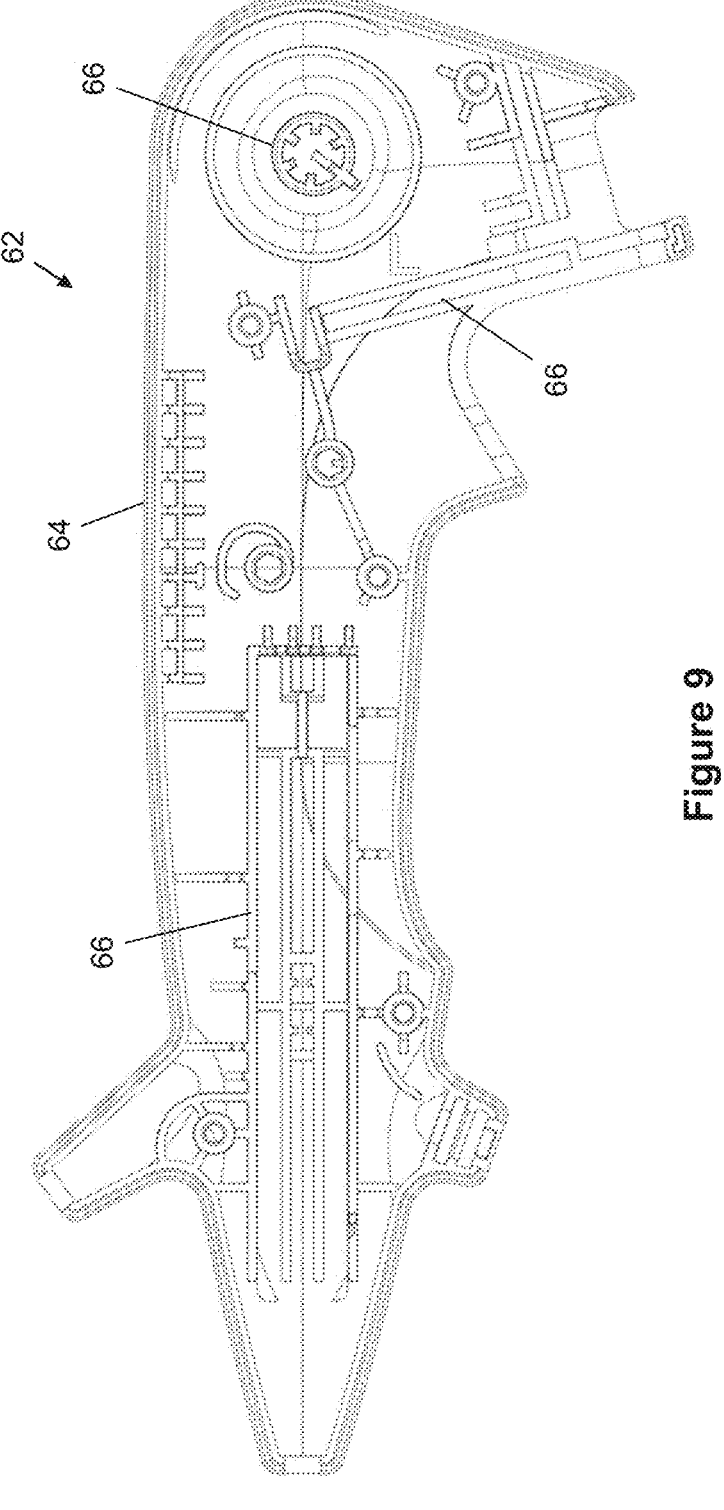
FIG. 9 is a side view of a shell forming part of a housing of the handle shown in FIG. 3.
Figure 10:
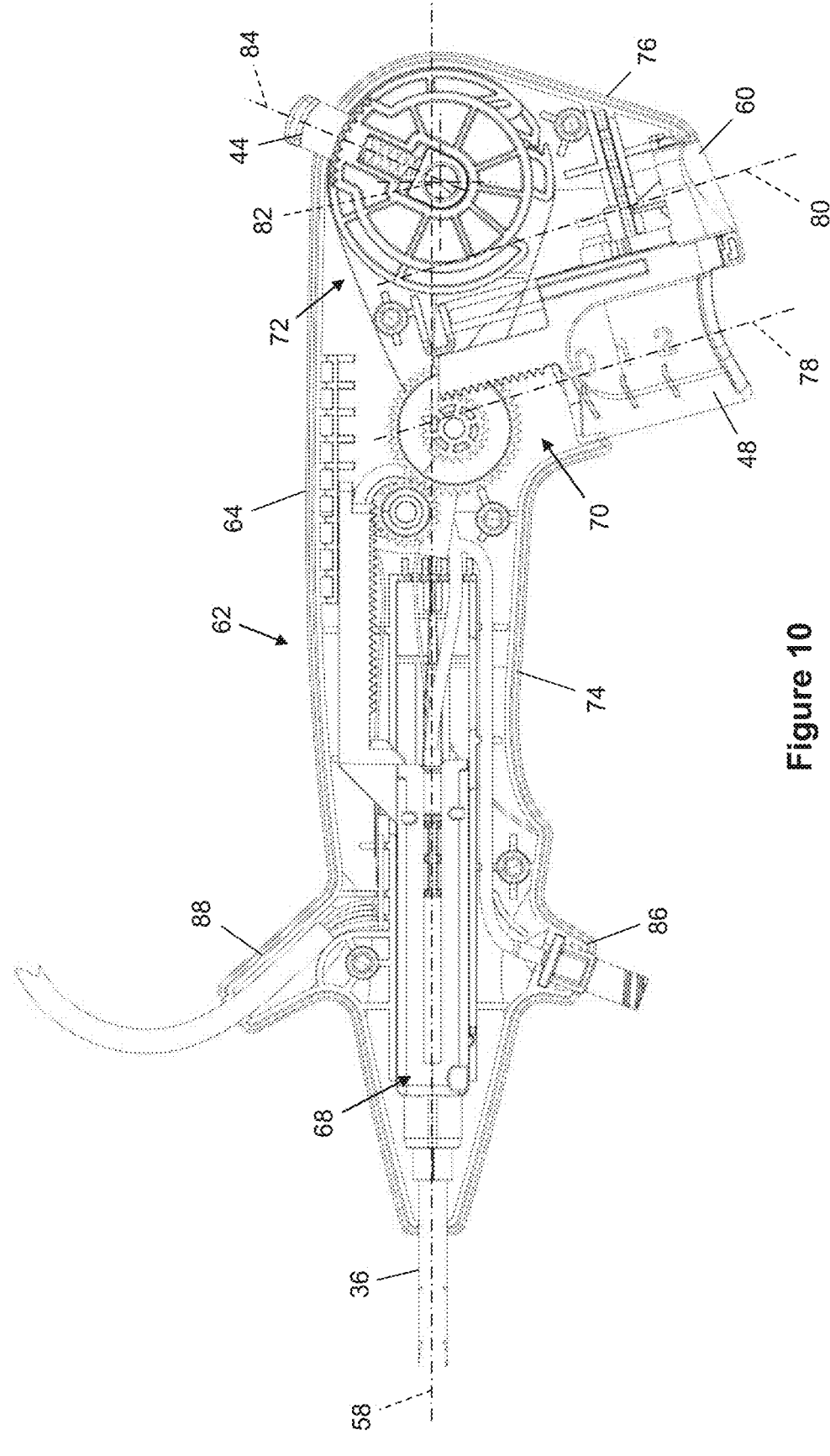
FIG. 10 corresponds to FIG. 9 but shows components of the handle fitted to the shell.

Turning next to FIGS. 9 and 10, the handle 34 comprises a hollow housing 62 of a moulded polymer material that is divided into two shells 64 along a central longitudinal plane according to one embodiment. The shells 64 are, substantially, mirror images of each other about the planar interface between the shells 64. The shells 64 are held together by screws that are spaced apart from each other and from components disposed within the housing 62.

On their concave inner sides, the shells 64 comprise integrally-moulded locating and guiding formations 66 that support and guide movement of various components disposed within and extending from the housing 62, as will be explained. As can be seen in FIG. 10, those components are grouped into various sub-assemblies, namely a hub assembly 68 at a proximal end of the delivery tube 36, a deployment system 70 that acts on the hub assembly 68 to drive longitudinal movement of specific elongate elements of the delivery tube 36 relative to each other, and a steering system 72 for deflecting a distal end portion of the delivery tube 36 when navigating to a deployment site in the patient's body. The hubs of the hub assembly 68 that are responsive to the deployment system 70 are movable relative to the housing 62 along the central longitudinal axis 58, which extends along and within the housing 62 in alignment with the proximal end of the delivery tube 36.

Viewed externally, the housing 62 of the handle 34 has a narrow waist 74 of approximately elliptical cross section and an enlarged proximal portion 76 at which user-operable control elements of the deployment system 70 and the steering system 72 protrude from within the handle 34 through respective openings in the housing 62.

Specifically, in one embodiment the control elements of the deployment system 70 are the deployment trigger 48 and the detent button 60, which are disposed beside each other. The deployment trigger 48 and the detent button 60 are movable into and out of the housing 62 along respective axes of operation, namely a trigger axis 78 and a detent axis 80, that are each transverse to the central longitudinal axis 58 of the housing 62. The trigger axis 78 and the detent axis 80 lie beside each other and are substantially straight and parallel in this example.

Conversely, in one embodiment the control element of the steering system 72 is the steering lever 44 that can be pivoted relative to the housing 62 about a pivot axis 82 within the housing 62. The pivot axis 82 is transverse to the central longitudinal axis 58 of the housing 62 and to the trigger axis 78 and a detent axis 80. The steering lever 44 can also move into and out of the housing 62 on a locking axis 84 that intersects the pivot axis 82, whereby pivotal movement of the steering lever 44 can be, respectively, unlocked and locked as will be explained.

Figure 11:
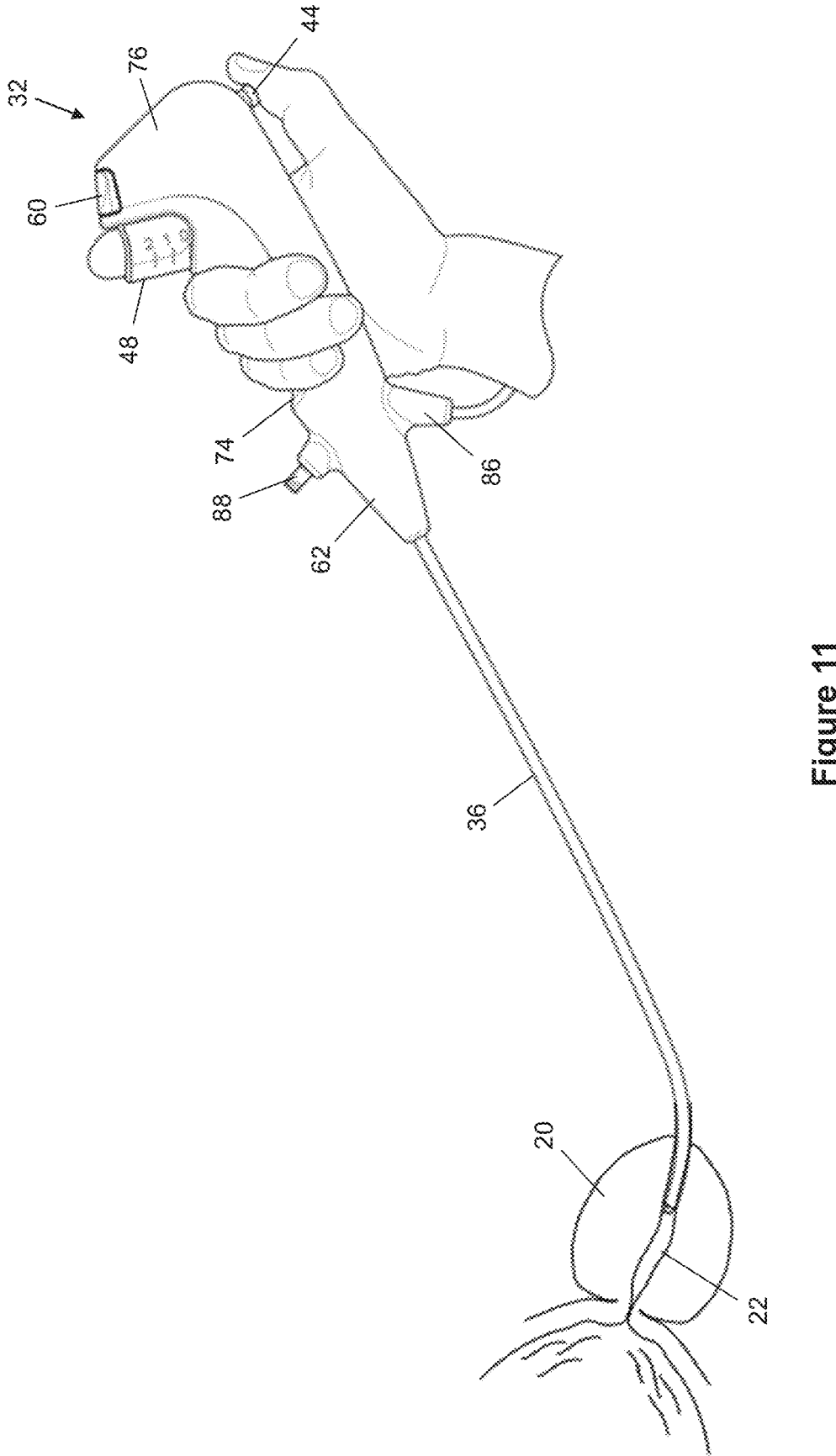
FIG. 11 is a schematic perspective view showing the device of the invention in use, with the distal end portion of the delivery tube advanced into a prostatic urethra and the handle held and operated by a user.

FIG. 11 shows that the device 32 is configured for largely one-handed operation and to allow a user to hold and to operate the device 32 using their left or right hand according to their preference in several embodiments. Consequently, the control elements of the deployment system 70 and the steering system 72, namely the deployment trigger 48, the detent button 60 and the steering lever 44, are disposed on, and are substantially symmetrical about, the central longitudinal plane that divides the shells 64 of the housing 62.

The device 32 is configured to be held by a user in an inclined or upright orientation in pistol-grip fashion. When holding the device 32 in that way, the user's forefinger or index finger aligns with, and so can easily operate, the deployment trigger 48 and the detent button 60 of the deployment system 70. Alternatively, the user could use their index finger to operate the detent button 60 and their second or middle finger to operate the deployment trigger 48. Conversely, the user's thumb aligns with, and so can easily operate, the steering lever 44 of the steering system 72 that protrudes from the opposite side of the housing 62 and is opposed to the deployment trigger 48 and the detent button 60 about the central longitudinal axis 58 of the housing 62.

The user's other fingers embrace the narrow waist 74 of the housing 62 to hold the device 32 in the palm of the hand while supporting the enlarged proximal portion 76 of the housing 62 above the palm. The delivery tube 36 therefore extends from the housing 62 initially in a generally downward distal direction but can bend from there along its length for its distal portion to follow a desired insertion path into the patient's prostatic urethra along the penile urethra.

The housing 62 further comprises an irrigation port 86 such as a Luer connector located distally with respect to the waist 74 of the housing 62 for conveying irrigation fluid into the delivery tube 36 from an external source. The housing 62 also comprises a power and data port 88 at a distal location opposed to the irrigation port 86. The power and data port 88 enables electrical power to be conveyed from an external power supply to imaging electronics of the delivery tube 36 and for image data to be conveyed from the imaging electronics to an external monitor.

Figure 12:
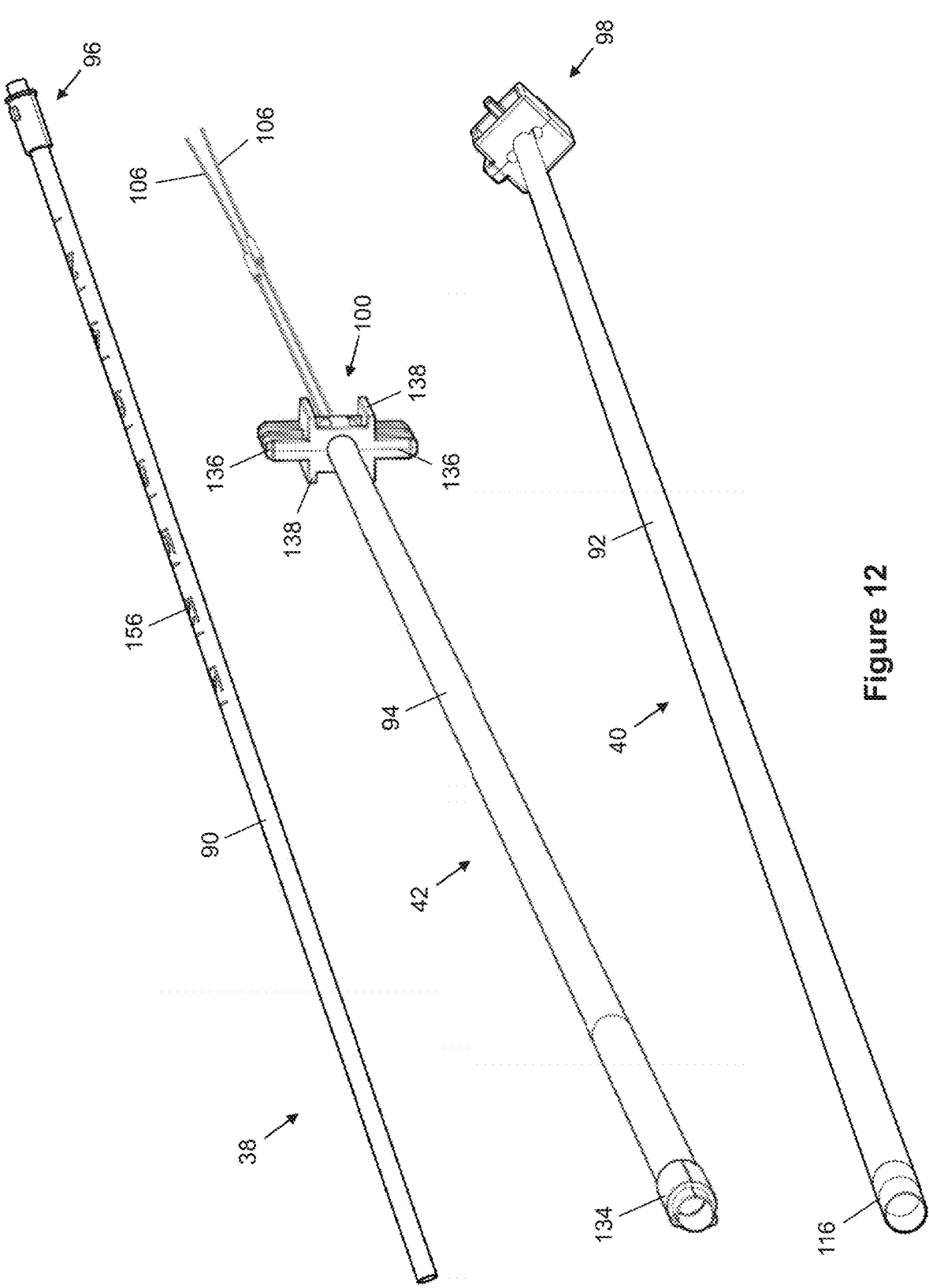
FIG. 12 is an exploded perspective view showing concentric elements of the delivery tube.

As noted above, the delivery tube 36 comprises three flexible tubular elements in concentric longitudinally-sliding relation, namely: an outer element 38 comprising an outer sheath 90; an inner element 40 comprising an imaging sheath 92; and an intermediate element 42 comprising a steering sheath 94 disposed in an annular gap defined between the outer sheath 90 and the imaging sheath 92. FIG. 12 shows those elements 38, 40, 42 separately. It will be apparent that each of the sheaths 90, 92, 94 is fixed to a respective hub 96, 98, 100 that is positioned at, or adjacent to, the proximal end of the associated element 38, 40, 42.

As will be explained, the intermediate element 42 is fixed against axial movement relative to the handle 34 whereas the outer and inner elements 38, 40 can move axially relative to both the intermediate element 42 and the handle 34. The hubs 96, 98, 100 lock the respective elements 38, 40, 42 within the system to prevent the outer and inner elements 38, 40 from moving in any direction except axially along a fixed travel path aligned with the central longitudinal axis 58 of the handle 34, as controlled by a user operating the deployment trigger 48 of the handle 34.

All of the sheaths 90, 92, 94 are tubular in this example although, in principle, the imaging sheath 92 could instead be a solid but flexible rod with any wiring, cabling or ducting embedded within it, for example in respective parallel channels of an extruded profile. In any event, any such wires or cables must be isolated from each other and from a flow of irrigating liquid that may be conveyed along the imaging sheath 92.

In several embodiments, the sheaths 90, 92, 94 should be as thin as possible to ensure that the overall diameter of the delivery tube assembly is advantageously small, for example with an outer diameter of less than sixteen French (5.33 mm) in the application described. As a non-limiting illustrative example, in one embodiment the outer sheath 90 may have a wall thickness of 0.159 mm to 0.254 mm, for example about 0.160 mm, 0.165 mm, 0.170 mm, 0.175 mm, 0.180 mm, 0.185 mm, 0.190 mm, 0.195 mm, 0.200 mm, 0.210 mm, 0.220 mm, 0.230 mm, 0.240 mm, 0.250 mm, etc. and values and ranges therein, whereas the main proximal section of the steering sheath 94 may have a wall thickness of about 0.394 mm to 0.464 mm (e.g., 0.400 mm, 0.410 mm, 0.420 mm, 0.430 mm, 0.440 mm, 0.450 mm, 0.460 mm, etc., and values and ranges therein), allowing about 0.61 mm for the expander 10 and for clearance. The wall thickness of the imaging sheath 92 under the expander 10 may, for example, be about 0.114 mm to 0.159 mm (e.g., 0.120 mm 0.130 mm, 0.140 mm, 0.150 mm etc. and values and ranges therein).

In several embodiments, the sheaths 90, 92, 94 are flexible enough to permit an angle of deflection along their full length of, for example, 40° to 90° (e.g., 45, 50, 60, 65, 70, 75, 80 degrees and values and ranges therein) so as to accommodate the curvature of the male urethral anatomy and to access the prostatic urethra 22. In particular, the sheaths 90, 92, 94 may be configured to be capable of flexing along their length as they extend along the urethra from the point of insertion at the penile meatus through to the bladder neck 24. The sheaths 90, 92, 94 therefore each have a flexible steering section to provide for deflection driven by a steering mechanism controlled by the steering system 72 of the handle 34 at the proximal end of the delivery tube 36 in several embodiments. The sheaths 90, 92, 94 may also each have a flexible proximal portion to provide for deflection imposed by the anatomy, for example to track through the curvature of the penile canal.

As an example, one or more of the sheaths 90, 92, 94 may be braided or coiled for flexibility to accommodate curvature of the anatomy and deflection of the imaging tip. However, the structure of the delivery tube 36 can also be stiff enough axially and circumferentially to resist the forces of insertion, steering, navigation, unsheathing of the expander 10 and, if necessary, re-sheathing of the expander 10. As explained below, any or all of the sheaths 90, 92, 94 may have tailored stiffness and flexion properties for these purposes.

In several embodiments, the torsional stiffness of the sheaths 90, 92, 94 may be sufficient to allow for angular alignment of the expander 10 about the central longitudinal axis 58. In this respect, the circumferential or angular positioning of the expander 10 within the prostatic urethra 22 is controlled by global rotation of the handle 34. In one embodiment, the handle 34 thereby applies torque to the sheaths 90, 92, 94 attached to it, noting that the sheaths 90,

92, 94 are fixed against circumferential angular movement relative to the handle 34 and so cannot rotate independently of the handle 34.

The simplest and most basic form of sheath would be a single extrusion comprising a polymer material of a certain durometer value. However, a single-material extrusion with the necessarily thin wall thickness may kink or buckle when deflected by a steering mechanism, or under axial compression, or under other bending loads. For this reason, any or all of the sheaths 90, 92, 94 may benefit from differential material properties along their length to provide the individual sheaths 90, 92, 94, and the stacked sheath assembly of the delivery tube 36, with the design characteristics required to access the prostatic urethra 22, to navigate the anatomy, and to steer and support the expander 10.

Examples of characterisation properties to be tailored along the length of a sheath 90, 92, 94 may include: flexibility; kink resistance; trackability; the ability to apply axial force parallel to the longitudinal axis 58—i.e. 'pushability'; and the ability to apply torque about the longitudinal axis 58—i.e. 'torquability'. Tailoring may, for example, be achieved by one or more of the following options:

Hybrid extrusion, in which two or more materials of differing stiffness or durometer properties are joined together by reflows or joints.

A fully-braided sheath, this being a custom multi-layered braided sheath with a specific pitch design or angle of braid that is tailored to the stiffness properties desired and/or required. Braiding may be uniform along its length.

A fully-braided coiled sheath, this being a custom multi-layered coiled sheath with a specific pitch design or angle of coil that is tailored to the stiffness properties desired and/or required. Coiling may be uniform along its length.

A hybrid braided sheath, this also being a custom multi-layered braided sheath with a specific pitch design or angle of braid tailored to the stiffness properties desired and/or required. However, in this case, braiding may be varied along its length, for example with tighter and looser braids, or denser and less dense braids, at different longitudinal positions where the sheath is required to be more or less flexible. The angle of the braids relative to central longitudinal axis 58 can also be varied to adjust flexibility along the length of a sheath.

A hybrid coiled sheath, this also being a custom multi-layered coiled sheath with a specific pitch design or angle of coil tailored to the stiffness properties desired and/or required. However, in this case, coiling may be varied along its length, for example with tighter and looser coils, or denser and less dense coils, at different longitudinal positions where the sheath is required to be more or less flexible. The angle of the coils relative to central longitudinal axis 58 can also be varied to adjust flexibility along the length of a sheath.

A hybrid of braided and coiled sheath, this also being a custom multi-layered braided and coiled sheath with certain sections of the sheath being braided, and certain sections of the sheath being coiled, with a specific pitch design or angle of braid and coil tailored to the stiffness properties desired and/or required. Braiding and coiling may be varied along its length, for example with tighter and looser braids/coils, or denser and less dense braids/coils, at different longitudinal positions where the sheath is required to be more or less flexible. The angle of the braids/coils relative to central longitudinal axis 58 can also be varied to adjust flexibility along the length of a sheath.

All of the above examples can have varying durometer of polymer jacket reflowed through the braid or coil wire where the sheath is required to be more or less flexible. Varying the thickness of this polymer can also be used to change the properties of the sheath where the sheath is required to be more or less flexible.

A rigid moulded tip section may be reflowed, bonded or over-moulded onto a braided sheath in various embodiments.

Figure 13:
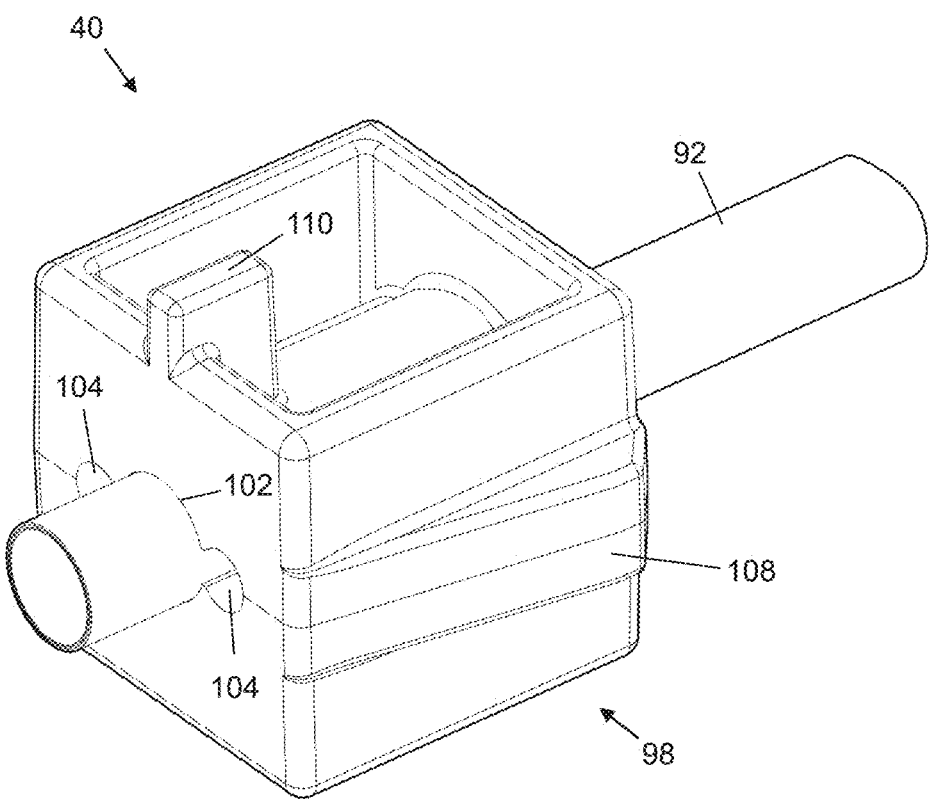
FIG. 13 is an enlarged perspective view of a proximal hub of an inner delivery tube element shown in FIG. 12.
Figure 14:
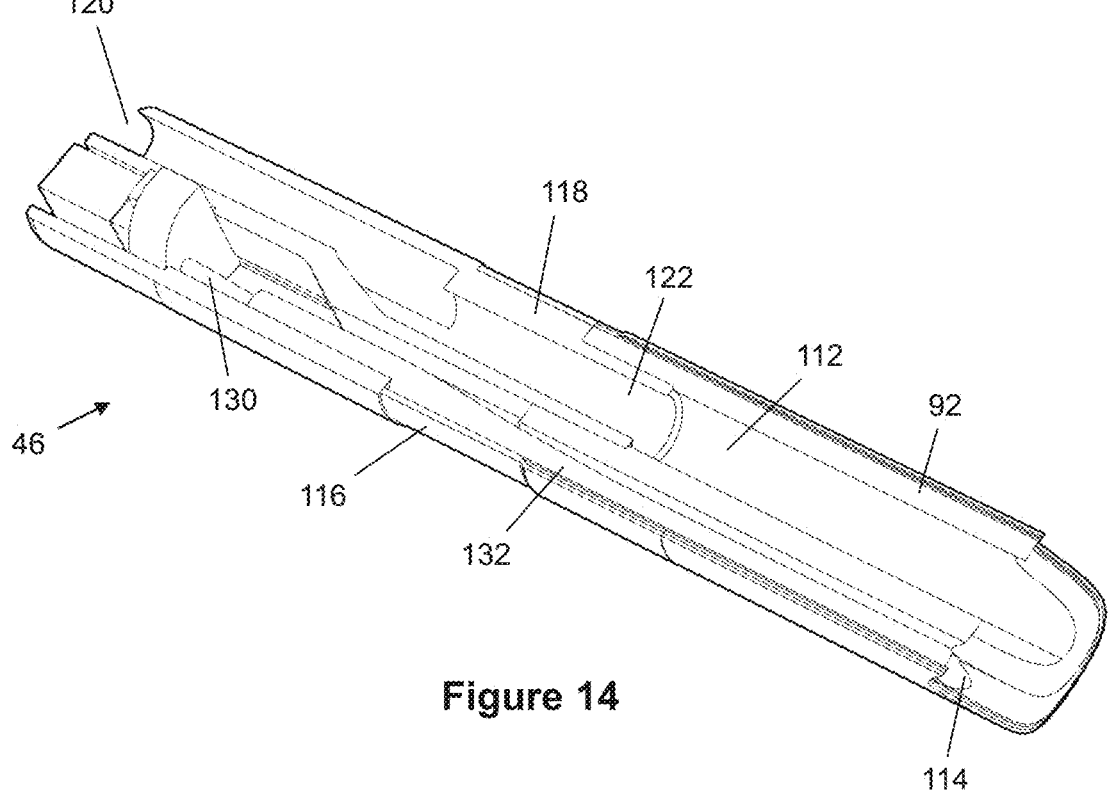
FIG. 14 is an enlarged cut-away distal perspective view of a camera tip that is attachable to a distal end of the inner delivery tube element shown in FIG. 12
Figure 15:
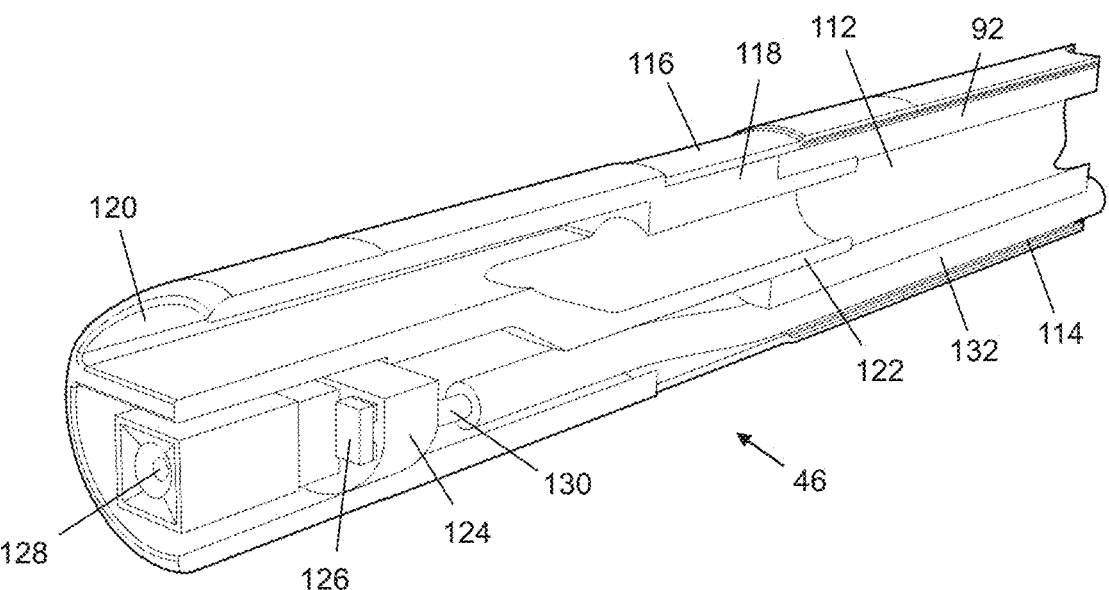
FIG. 15 is an enlarged cut-away proximal perspective view of the camera tip shown in FIG. 14.

Referring now also to FIG. 13, the inner element 40 comprises the imaging sheath 92 and an inner element hub 98 that is fixed to the imaging sheath 92 adjacent to a proximal end of the imaging sheath 92. Conversely, FIGS. 14 and 15 show the moulded camera tip 46 that is fixed to a distal end of the imaging sheath 92 and also forms part of the inner element 40, although the camera tip 46 is not shown in FIG. 13.

The inner element hub 98 protrudes laterally from the imaging sheath 92. The imaging sheath 92 extends through the inner element hub 98 in this example, although it would be possible instead for the imaging sheath 92 to terminate at or within the inner element hub 98. The inner element hub 98 is overmoulded onto the imaging sheath 92 but could instead, or additionally, be bonded or welded to the imaging sheath 92 and/or could be an interference fit around the imaging sheath 92.

In this example, the inner element hub 98 is generally cuboidal, receiving the imaging sheath 92 in a through-bore 102 that is centred on mutually-parallel proximal and distal faces of the inner element hub 98. The inner element hub 98 is also penetrated by a pair of parallel side bores 104 extending between the proximal and distal faces, one each side of the central through-bore 102. The side bores 104 accommodate a pair of steering wires 106 extending proximally from the intermediate element 42 of the delivery tube 36, as shown in FIG. 12 and as will be explained further.

Opposed side faces of the inner element hub 98, generally orthogonal to the proximal and distal faces, lie generally parallel to each other and to the longitudinal axis of the imaging sheath 92. A wedge formation 108 protrudes laterally from one of the side faces and tapers proximally from a distal shoulder to intersect that side face.

The proximal face of the inner element hub 98 is surmounted by a lug 110 that projects from the inner element hub 98 orthogonally with respect to the longitudinal axis of the imaging sheath 92. The lug 110 ensures that the inner element hub 98 is oriented correctly when being incorporated into the hub assembly 68, so that the wedge formation 108 on one of the side faces protrudes from the correct side of the hub assembly 68.

The imaging sheath 92 also shown in FIGS. 14 and 15 contains an irrigation channel and an electronics channel 114 that are disposed beside each other in parallel relation. Specifically, the irrigation channel is defined by an irrigation tube 112 that is offset laterally within the lumen of the imaging sheath 92, whereas the electronics channel 114 is defined in the space remaining within that lumen beside the irrigation tube 112. The irrigation tube 112 is fluidly connected to the irrigation port 86 in the handle 34 whereby irrigating liquid can travel from the proximal end to the distal end of the imaging sheath 92.

Close sliding contact between the inner element 40 and the intermediate element 42 is desirable to maintain a tight seal to minimise ingress of liquids into the distal end of the delivery tube 36 between the inner and intermediate elements 40, 42.

FIG. 13 shows that the inner element 40 comprises a socket 116 at the distal end of the imaging sheath 92. The camera tip 46 shown in FIGS. 14 and 15 comprises a proximal outer spigot 118 that is received in the socket 116. The camera tip 46 also defines a distally-facing irrigation outlet 120 in fluid communication with the irrigation tube 112. For this purpose, the camera tip 46 comprises a proximal tubular inner spigot 122 that is received in the distal end of the irrigation tube 112. The irrigation channel thereby extends longitudinally from the irrigation tube 112 through the camera tip 46 from the inner spigot 122 to the irrigation outlet 120.

Within the camera tip 46, the irrigation channel has a dog-leg shape that offsets the irrigation outlet 120 laterally from the longitudinal axis of the irrigation tube 112. The irrigation outlet 120 is thereby offset laterally from, and disposed beside, a distally-opening recess that houses a PCB 124, light emitters 126 such as LEDs and a CMOS imaging chip 128 exposed at the distal end of the camera tip 46. The light emitters 126 are disposed beside the imaging chip 128, preferably one on each side of the CMOS chip 128.

The ratio of the length of the internal space in the camera tip 46 to the length of the PCB 124 and the CMOS chip 128 is such that CMOS chip 128 does not sit inside the camera tip 46, at least to the extent that the field of view of the CMOS chip 128 could otherwise be limited by the camera tip 46. Thus, the CMOS chip 128 is preferably at, or least substantially flush with, the distal end of the camera tip 46.

A cable 130 extending along the electronics channel 114 beside the irrigation tube 112 conveys power from the power and data port 88 of the housing 62 to the PCB, LEDs and the imaging chip and conveys image data from the imaging chip back along the inner element 40 to the power and data port. In this example, the cable 130 is surrounded by a protective sleeve 132 and is received in a longitudinal groove formed externally in the wall of the irrigation tube 112.

Returning to FIG. 12, the intermediate element 42 comprises the steering sheath 94, an intermediate element hub 100 that is fixed to a proximal end of the steering sheath 94, and a moulded steering tip 134 that is fixed to a distal end of the steering sheath 94. The steering sheath 94 lies on and surrounds the imaging sheath 92, leaving a distally-protruding portion of the imaging sheath 92 defined by the camera tip 46 exposed.

The intermediate element hub 100 comprises integrally-moulded tabs 136 that are diametrically opposed about, and extend radially from and parallel to, the longitudinal axis of the steering sheath 94. As will be explained, these projecting tabs 136 are received in complementary formations of the housing 62 of the handle 34 to locate the intermediate element 42 against axial and circumferential movement relative to the handle 34. Additionally, integrally-moulded pairs of projections 138 extend laterally from mutually-opposed sides of the intermediate element hub 100 between the opposed tabs 136. In this example, the intermediate element hub 100 is overmoulded onto the steering sheath 94 but could instead, or additionally, be bonded or welded to the steering sheath 94 and/or could receive the steering sheath 94 as an interference fit.

Figure 16:
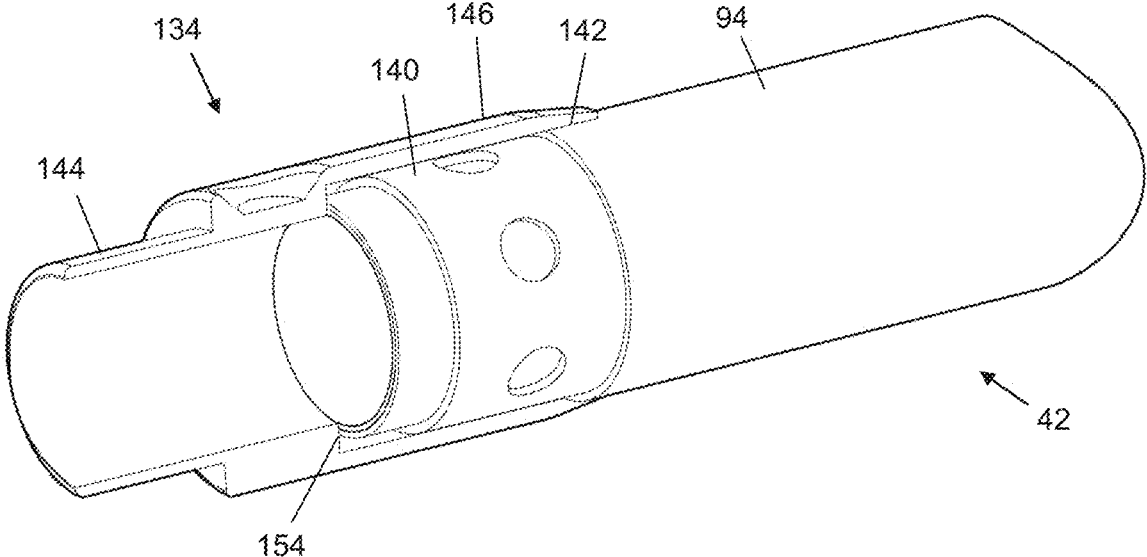
FIG. 16 is an enlarged cut-away distal perspective view of a steering tip at a distal end of an intermediate delivery tube element shown in FIG. 12.
Figure 17:
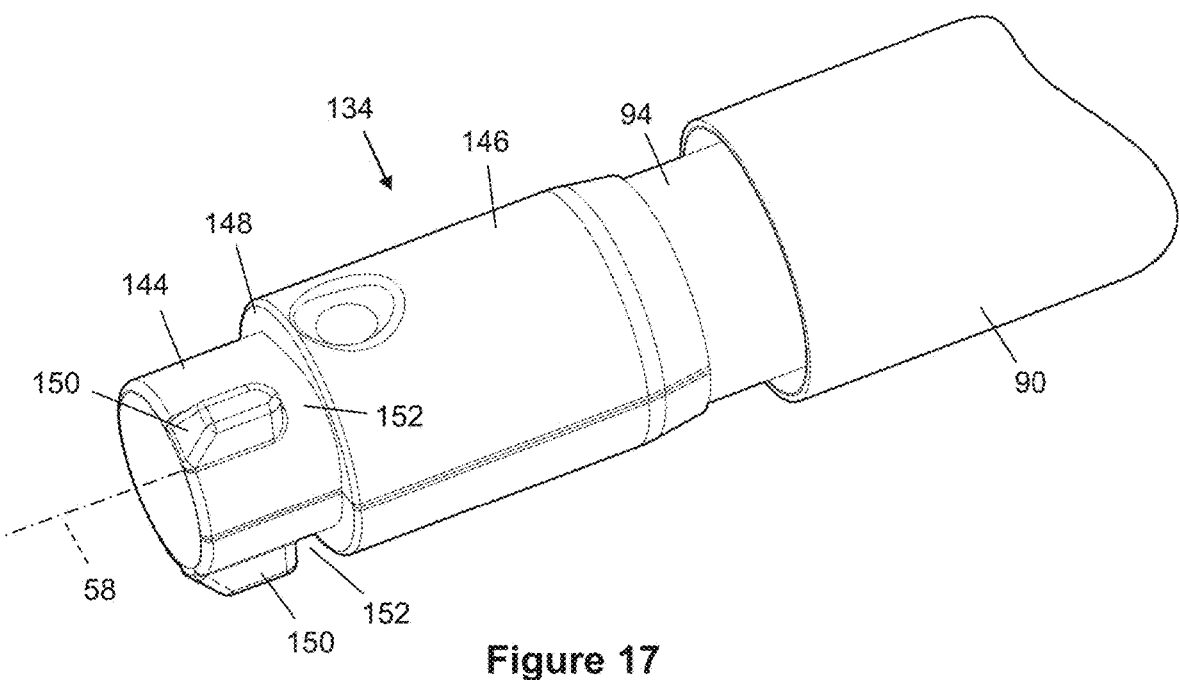
FIG. 17 is an enlarged distal perspective view of the steering tip shown in FIG. 16.

Turning now also to FIGS. 16 and 17, the intermediate element 42 further comprises a rigid steering pull ring 140 that is oriented circumferentially within the distal end of the steering sheath 94, initially in axial alignment with the central longitudinal axis 58 of the steering sheath 94. In this example, the steering ring 140 is embedded or encased within the tubular wall of the steering sheath 94, sandwiched between inner and outer layers of the steering sheath 94. The steering tip 134 is overmoulded onto, or bonded over, the distal end portion of the steering sheath 94 so as to receive, encircle and engage with the steering ring 140 within a socket 142 formed in a proximal portion of the steering tip 134.

The steering ring 140 and the steering tip 134 lie at the interface between the imaging sheath 92 and the steering sheath 94 and facilitate longitudinal movement of the imaging sheath 92 relative to the steering sheath 94. In particular, the imaging sheath 92 slides longitudinally within and with respect to the steering sheath 94, the steering ring 140 and an implant holder defined by the steering tip 134.

The pair of steering wires 106 acting on mutually-opposed sides of the steering ring 140 extend proximally in parallel relation along the steering sheath 94 in mutual opposition about the central longitudinal axis 58. Like the steering ring 140, the steering wires 106 are embedded within the tubular wall of the steering sheath 94, for example enmeshed with or threaded through a braided structure of that wall. The steering wires 106 extend proximally from the steering ring 140 along the steering sheath 94 and through the intermediate element hub 100 to protrude proximally from the intermediate element hub 100, where they are crimped to corresponding wires of the steering system 72. As mentioned above, the steering wires 106 extend through the parallel side bores 104 of the inner element hub 98 when the intermediate element hub 100 and the inner element hub 98 are brought together in the hub assembly 68.

In use of the device 32, increased tension applied selectively by the steering system 72 to one of the steering wires 106 pulls on the associated side of the steering ring 140, hence tilting the steering ring 140 away from axial alignment with the central longitudinal axis 58. The steering tip 134 also tilts with the steering ring 140 by virtue of the engagement of the steering ring 140 within the socket 142 of the steering tip 134.

Consequently, the steering sheath 94 bends along its length toward the steering wire 106 that is under greater tension, similarly forcing the outer sheath 90 and the imaging sheath 92 of the delivery tube 36 to bend along their length. These concentric elements of the delivery tube 36 bend together preferentially at a distal longitudinal position with respect to the steering sheath 94, immediately proximal of the steering ring 140. The intrados of that bend corresponds to the steering wire 106 that is under greater tension and the extrados of that bend corresponds to the steering wire 106 that is under lesser or no tension.

The steering tip 134 serves, in use, as a holder for an implant such as an expander 10. For this purpose, the steering tip 134 has a longitudinally-stepped profile such that its distal portion 144 is narrower than its proximal portion 146. A radially outer side of the distal portion 144 defines a cylindrical support surface of lesser diameter whereas a radially outer side of the proximal portion 146 defines a cylindrical bearing surface of greater diameter. More specifically, the proximal portion 146 of the steering tip 134 is radially oversized relative to the diameter of the steering sheath 94 so that the bearing surface stands proud of the steering sheath 94. It is desirable that the steering sheath 94 is no wider than the proximal portion 146 of the steering tip 134 so as to facilitate telescopic insertion of the intermediate element 42 into the outer element 38 during assembly of the delivery tube 36. In this example, the proximal portion 146 of the steering tip 134 also has a chamfered proximal edge to ease assembly.

Whilst the concentric sheaths of the delivery tube 36 may slide past each other with minimal frictional resistance, the proximal portion 146 of the steering tip 134 may optionally help to facilitate sliding movement of the outer sheath 90 relative to the steering sheath 94.

In more detail, with particular reference to FIG. 17, the distal portion 144 of the steering tip 134 that defines the support surface comprises a support tube extending distally beyond the steering sheath 94, integral with and of lesser outer diameter than the proximal portion 146 of the steering tip 134. A circumferential step 148 effects a sharp reduction in the outer diameter of the steering tip 134 from the proximal portion 146 to the distal portion 144. The step 148 corresponds to a circumferential shoulder between the proximal portion 146 and the distal portion 144 that lies in a plane substantially orthogonal to the longitudinal axis of the steering sheath 94.

In several embodiments, one or more angularly-spaced implant retention formations (e.g., implant retainer formations), exemplified here by retaining lugs 150, protrude radially from the distal portion 144 of the steering tip 134. In various embodiments, one, two, three, four, five or more implant retainer formations, such as lugs 150, are provided. The height or radial protrusion of the retaining lugs 150 is the same as, or slightly less than, the height of the step 148 defined by the radial extent of the shoulder beyond the distal portion 144. Conversely, the thickness of the wire of the expander 10 is slightly less than the height of the step 148. The expander 10 extends from a proximal end where it is supported by the distal portion 144 of the steering tip 134 to a distal end where it is supported by the camera tip 46 of the imaging sheath 92 in deployment stage zero. The retaining lugs 150 hold the expander 10 against axial and circumferential movement relative to the steering sheath 94.

In one embodiment, for example, there are two retaining lugs 150 both offset to one side of the central longitudinal axis 58 of the steering sheath 94, with mutual circumferential spacing. The lugs 150 of that pair are spaced apart from each other by a lesser sector spanning about 120° of arc to one side of the steering tip 134 and conversely by a larger sector spanning about 240° of arc to the other side of the steering tip 134. A third proximal apex of the expander 10 is accommodated between the lugs 150 in the larger of those gaps.

The retaining lugs 150 are spaced distally from the shoulder defined by the step 148 of the steering tip 134, defining slots or gaps 152 between the lugs 150 and the shoulder. Those gaps 152 receive respective proximal apices 16 of an expander 10 supported by the device 32 when the expander 10 is held against the support surface of the distal portion 144 by the outer sheath 90. Thus, the thickness of the wire of the expander 10 is slightly less than the length of the gaps 152 between the lugs 150 and the step 148. The shoulder defined by the step 148 therefore serves as an additional proximal retention formation that cooperates with the retaining lugs 150, holding the proximal apices 16 of the expander 10 between the shoulder and the respective lugs 150 against axial movement relative to the steering tip 134.

The retaining lugs 150 are also received between struts 18 of the expander 10 that converge to the respective proximal apices 14. Thus, the retaining lugs 150 locate the expander 10 against circumferential or angular movement relative to the steering tip 134.

By virtue of the retaining lugs 150 and the shoulder defined by the step 148, the expander 10 is located against axial and angular movement relative to the handle 34, save to the extent that the distal end of the steering sheath 94, and hence the steering tip 134 and the expander 10, can be deflected relative to the handle 34 by operating the steering system 72.

Internally, as shown in FIG. 16, the steering tip 134 has a circumferential shoulder 154 that effects a step change in the diameter of its longitudinal lumen from the wider proximal portion 146 to the narrower distal portion 144. The internal diameter of the distal portion 144 is a sliding fit with the imaging sheath 92, which slides longitudinally within and relative to the distal portion 144.

The proximal portion 146 of the steering tip 134 accommodates the steering ring 140 as an interference fit. The steering ring 140 could also, or alternatively, be secured in the steering tip 134 by a bonding or welding process suitable for polymers, such as reflow or over-moulding. Adhesives and curing could also be used. The distal end of the steering ring 140 faces or abuts the proximally-facing internal shoulder 154.

Thus, this example has an implant holding and steering feature in the form of the steering tip 134 that not only holds the expander 10 but can also steer the expander 10 and therefore the sheaths that support the expander 10. In this respect, it is advantageous to steer from behind the expander 10, i.e. at a position that is proximal relative to the expander 10, so as to guide the expander 10 forward through the anatomy to the deployment location.

In proximal succession from the expander 10, therefore, the steering sheath 94 fitted with the steering ring 140 and the steering tip 134 provides: holding features that hold and orient the expander 10; a steering mechanism acting on a flexible steering section; and a flexible proximal portion to track through the penile canal. In conjunction with the imaging sheath 92 and the outer sheath 90, the structure of the steering sheath 94 must provide sufficient tensile or axial strength for unsheathing and re-sheathing the expander 10 and to allow for deflection of the expander 10 through all stages of deployment. The structure of the steering sheath 94 must also provide sufficient torsional strength to orient the expander 10 angularly about its central longitudinal axis 58 in response to corresponding angular manipulation of the handle 34 by a user.

Returning once again to FIG. 12, the outer element 38 comprises a tubular outer sheath 90 and an outer element hub 96 that is mounted on the outer sheath 90 at or near its proximal end. The outer sheath 90 comprises a distal tip portion that may be coiled rather than braided to improve retention of the expander 10 and to conform to steering deflection and a flexible proximal portion to facilitate navigation of the delivery tube 36, including steering movements of the delivery tube 36 driven by deflection of the steering sheath 94 disposed within the outer sheath 90. The outer sheath 90 also has a series of graduated and numbered external markings 156 along its proximal portion as a guide to the depth of insertion of the delivery tube 36 into the penile urethra.

Figure 18:
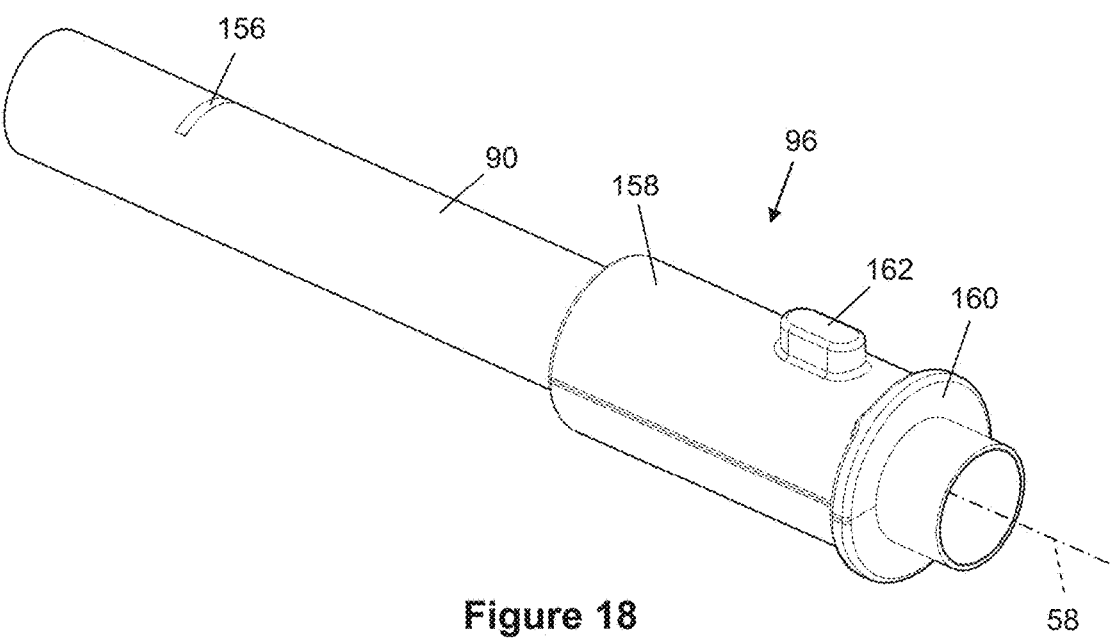
FIG. 18 is an enlarged perspective view of a proximal hub of an outer delivery tube element shown in FIG. 12.

As best appreciated in FIG. 18, the outer element hub 96 comprises a tubular body 158 of circular cross-section that is concentric with the outer sheath 90. In this example, the outer element hub 96 is overmoulded onto the outer sheath 90. In other examples, the outer sheath 90 could extend within the outer element hub 96 as an interference fit or could instead, or additionally, be bonded or welded to the outer element hub 96.

Integrally-moulded locating formations protrude from the body 158 of the outer element hub 96, namely: a proximal flange 160 that encircles the body 158 and lies in a plane orthogonal to a central longitudinal axis 58 of the outer sheath 90; and an elongate radially-protruding lug 162 that extends in a plane containing that axis 58. These locating formations 160, 162 are received in complementary formations at a distal end of a hub casing 164 of the hub assembly 68 to locate the outer element 38 against axial and circumferential movement relative to the hub assembly 68. In several embodiments, a hub casing 164 serves as a hub carriage. In several embodiments, a hub casing 164 is a hub carriage.

Figure 19A:
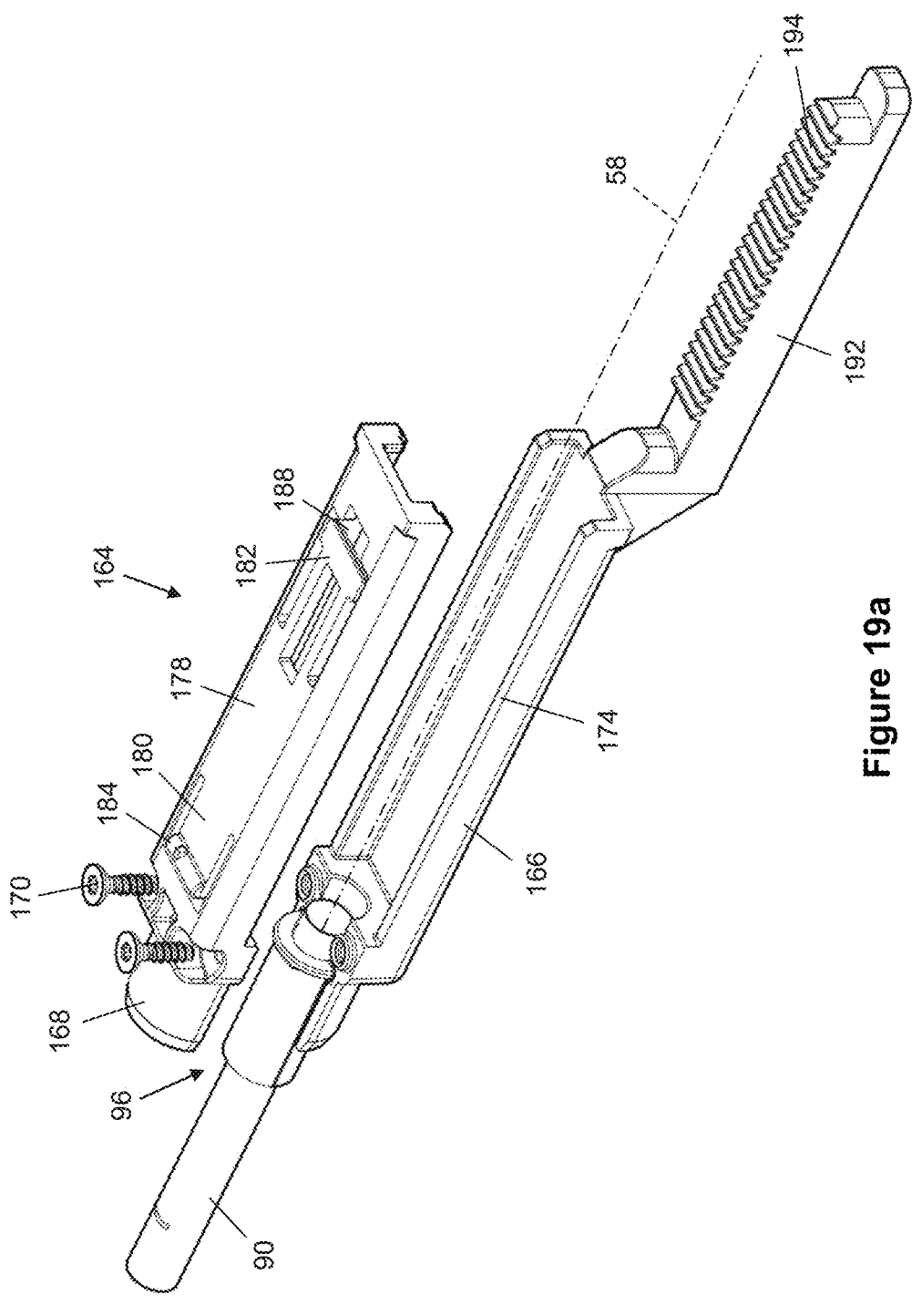
FIGS. 19*a* and 19*b* are exploded perspective views of a hub casing attached to the proximal hub of the outer delivery tube element shown in FIG. 18.
Figure 19B:
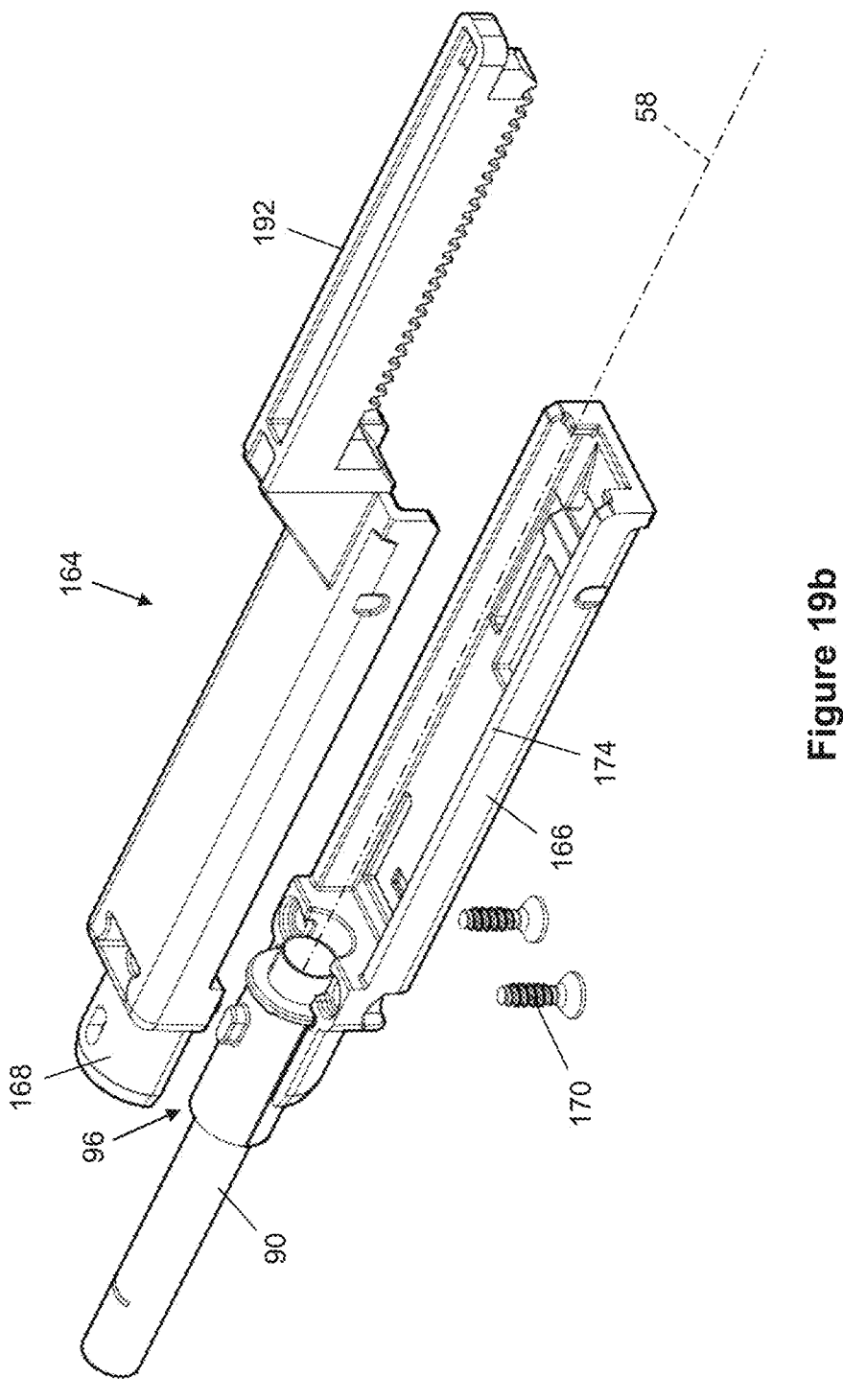

Moving on, therefore, to FIGS. 19a and 19b, the hub casing 164 of the hub assembly 68 is an elongate hollow enclosure that extends along the central longitudinal axis 58 of the housing 62 of the handle 34, in alignment with the corresponding axis of the delivery tube 36. The hub casing 164 comprises a generally cuboidal body 166 and an integral open-ended tubular extension 168 that extends distally from the body 166, the tubular extension 168 being centred on the central longitudinal axis 58 and communicating with the interior of the body 166.

The hub casing 164 is divided into two casing parts along a central longitudinal plane that bisects the tubular extension 168 and a pair of mutually-opposed side faces of the cuboidal body 166. The casing parts are brought together in mutual opposition about their planar interface and fastened together. In this example, the casing parts are fastened together by screws 170, one each side of the central longitudinal axis 58, at the junction between the body 166 and the tubular extension 168 of the hub casing 164.

Thus assembled, the hub casing 164 receives, encloses and retains the hubs 96, 98, 100 of the outer element 38, the intermediate element 42 and the inner element 40 of the delivery tube 36. The outer element hub 96, the intermediate element hub 100 and the inner element hub 98 are thereby disposed within the hub casing 164 in proximal succession. The hub casing 164 supports the outer element hub 96 at a distal end and the inner element hub 98 at a proximal end, and has a longitudinally-extending intermediate portion that connects the distal and proximal ends and bridges around the intermediate element hub 100.

The tubular extension 168 of the hub casing 164 defines an internal channel of circular cross-section that is a close fit around the body 158 of the outer element hub 96. The screws 170 that fasten together the casing parts can serve to clamp the outer element hub 96 between the distal ends of the casing parts that define the tubular extension 168.

The tubular extension 168 of the hub casing 164 also has internal locating formations that are complementary to the external locating formations of the outer element hub 96. Specifically, the flange 160 of the outer element hub 96 is received in a circumferential groove within the tubular extension 168 to prevent axial movement of the outer element 38 relative to the hub casing 164. Thus, the outer element 38 of the delivery tube 36 is constrained always to move with the hub casing 164 in longitudinal directions relative to the housing 62 of the handle 34. Similarly, the lug 162 of the outer element hub 96 is received in a longitudinal slot within the tubular extension to lock the outer element 38 against angular movement relative to the hub casing 164 about the central longitudinal axis 58.

Figure 20:
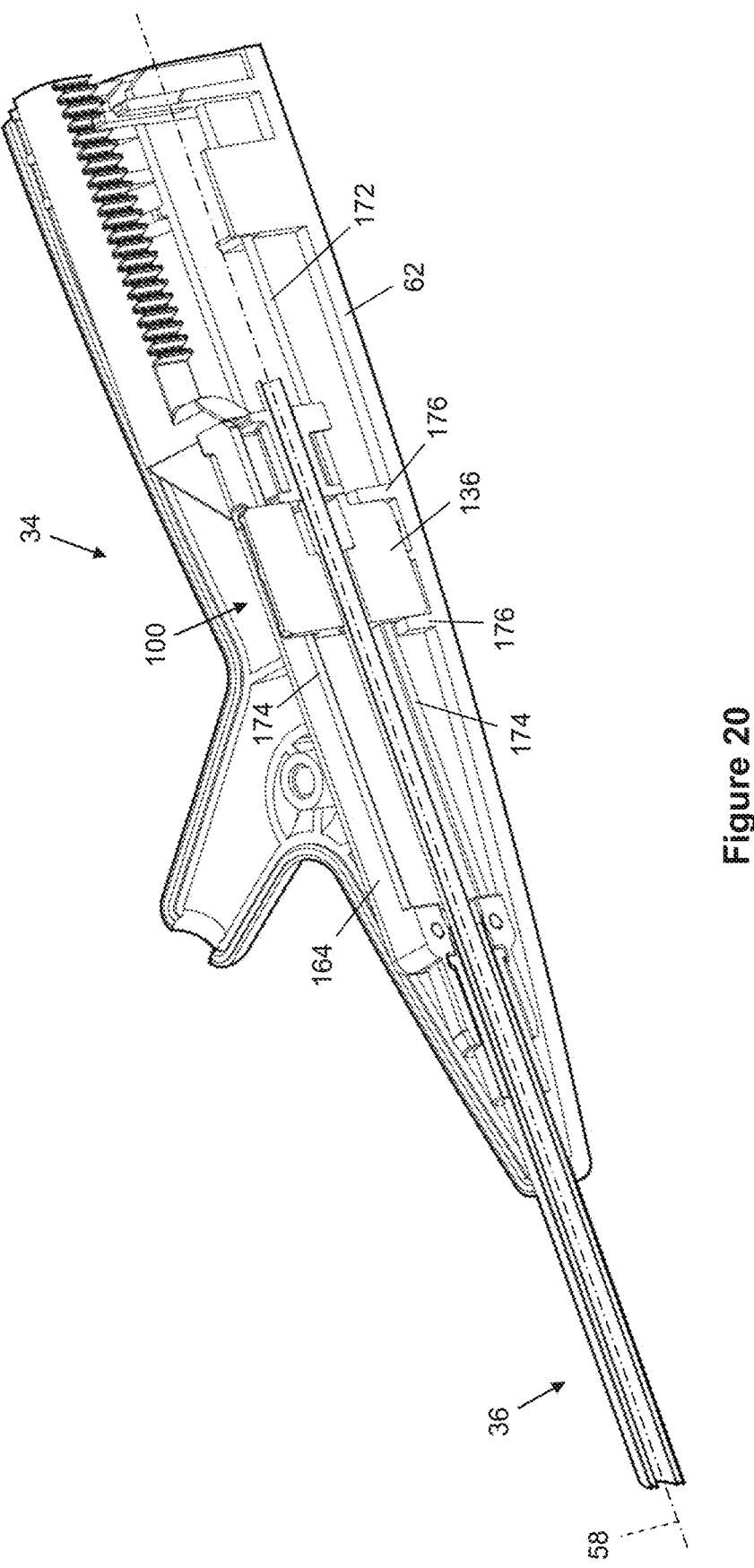
FIG. 20 is a cut-away perspective view of a proximal hub of an intermediate delivery tube element shown in FIG. 12, shown engaged with the housing of the handle.

Referring now also to FIG. 20, the outer and inner elements 38, 40 of the delivery tube 36 can move axially relative to both the intermediate element 42 and the handle 34 as noted previously. For this purpose, the hub casing 164 is movable reciprocally through a stroke range along the central longitudinal axis 58 within, and relative to, the housing 62. The hub casing 164 is supported between, and is slidably movable along, longitudinally-extending parallel rail formations 172 that are moulded integrally into the inner face of each shell 64 of the housing 62. The hub casing 164 thereby serves as a carriage for the outer element hub 96 and for the inner element hub 98, carrying those hubs 96, 98 for movement along a retraction path that extends longitudinally within the housing 62, parallel to the central longitudinal axis 58.

Conversely, as also noted previously, the intermediate element 42 of the delivery tube 36 is fixed against axial movement relative to the handle 34. Consequently, provision is made for the hub casing 164 to move longitudinally around, and relative to, the intermediate element hub 100 that is accommodated within the body 166 of the hub casing 164. For this purpose, the facing edges of the casing parts are cut away at their planar interface to define mutually-opposed longitudinal slots 174 when the casing parts are assembled together. Each slot 174 has a closed distal end and an open proximal end.

With reference to FIG. 20, the slots 174 penetrate the aforementioned pair of side faces of the body of the hub casing 164 to accommodate the diametrically-opposed tabs 136 that extend laterally from the intermediate element hub 100. Those tabs 136 protrude from the hub casing 164 through the slots 174 to engage in respective socket formations 176 that are moulded integrally into the inner face of each shell 64 of the housing 62. In this way, the intermediate element hub 100 is locked against axial or angular movement relative to the housing 62, while the slots 174 provide clearance around the tabs 136 for the hub casing 164 and the outer and inner element hubs 96, 98 to move longitudinally relative to the intermediate element hub 100. The hub casing 164 slides over the aforementioned projections 138 of the intermediate element hub 100 disposed between the opposed tabs 136, which maintain lateral alignment between the hub casing 164 and the intermediate element hub 100.

Returning to FIG. 19a, the cuboidal body 166 of the hub casing 164 has a further side face 178 disposed between the slotted pair of side faces. That further side face 178 is penetrated by slits in a C-shaped arrangement that define resiliently-deflectable tongues 180, 182 formed integrally with the body. One of those tongues 180 is at a distal location on the side face 178 and another of those tongues 182 is at a proximal location on the side face 178.

Figure 21A:
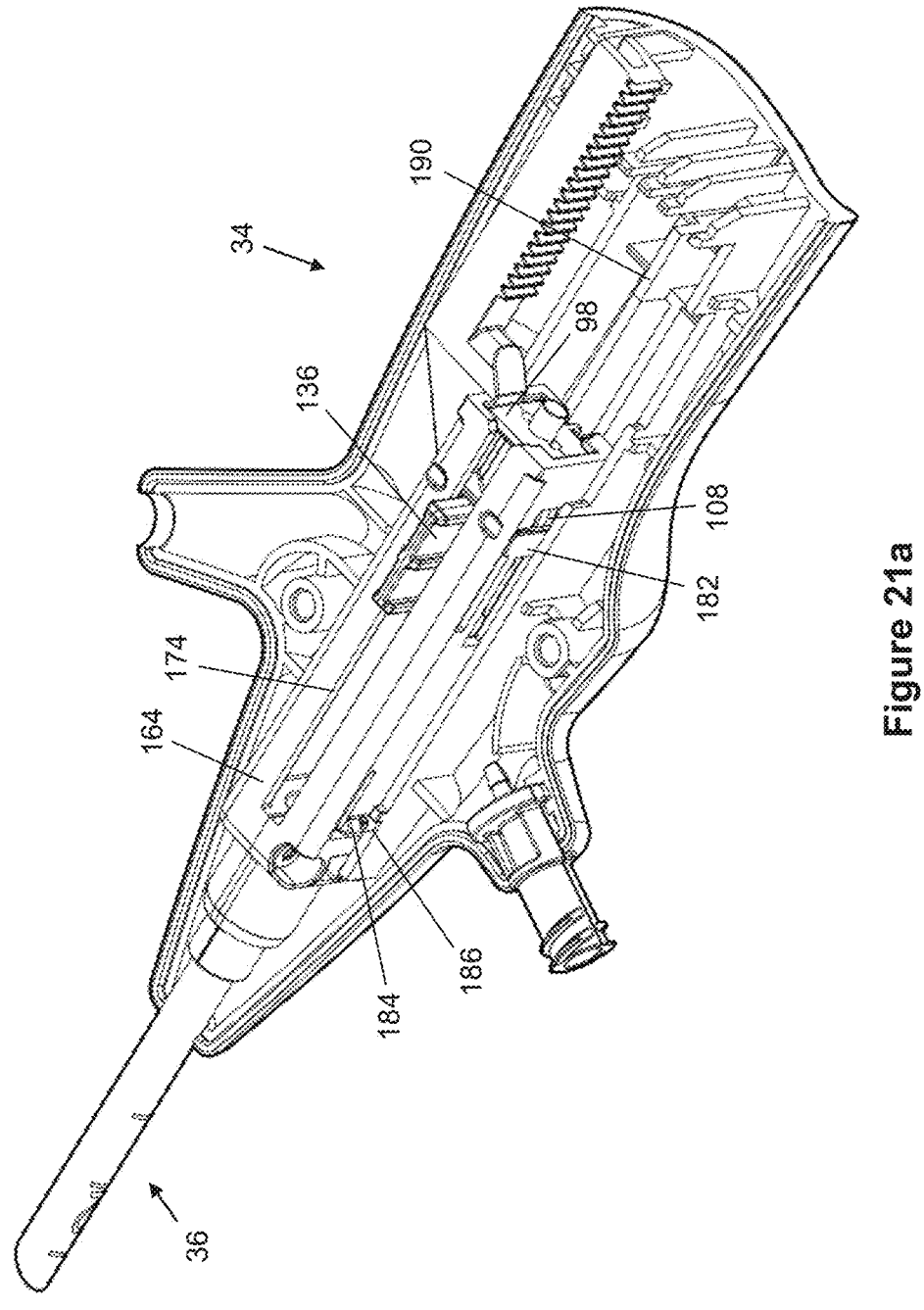
FIGS. 21*a* to 21*d* are a sequence of cut-away perspective views showing movement of the hub casing of FIGS. 19*a* and 19*b* relative to the housing of the handle between various deployments stages of the device.

The distal tongue 180 has an integral flange 184 at its distally-facing free end that protrudes outwardly from the surrounding side face 178 of the body 166. As shown in FIG. 21a, the flange 184 snap-engages in a complementary inwardly-facing groove 186 in the adjacent rail formation of the housing 62 that guides longitudinal movement of the hub casing 164 relative to the handle 34. Engagement between the flange and the groove latches the hub casing 164 against that longitudinal movement. This is to prevent inadvertent retraction of the outer element 38 of the delivery tube 36, hence transitioning the device 32 from deployment stage zero to deployment stage one, until a user applies enough force to the deployment trigger 48 to effect that transition deliberately. In that case, as shown in FIG. 21b, the distal tongue deflects 180 inwardly to disengage the flange 184 from the groove 186, thereby to free the hub casing 164 for movement relative to the housing 62.

Returning again to FIG. 19a, the proximal tongue 182 lies flush with the surrounding side face 178 of the body 166 but the transverse slit 188 at its proximally-facing free end is enlarged to receive and engage with the aforementioned wedge formation 108 on a side face of the inner element hub 98. Initially, that engagement holds the inner element hub 98 at the proximal end of the hub casing 164. In this way, with reference to FIGS. 21a to 21c, the inner element hub 98 is constrained to move with the hub casing 164 and with the outer element hub 96 as the device 32 transitions from deployment stage zero to deployment stage one. In the same way, the inner element hub 98 is constrained to move with the hub casing 164 and with the outer element hub 96 if the device 32 is returned from deployment stage one to deployment stage zero.

Unlike the outer element hub 96, the inner element hub 98 is not fixed to the surrounding hub casing 164 but can instead move relative to the hub casing 164 within a limited longitudinal range. With reference to FIG. 21*d*, this enables movement of the outer element hub 96, and therefore the outer sheath 90, to be decoupled from movement of the inner element hub 98, and therefore the imaging sheath 92, as the device 32 transitions from deployment stage one to deployment stage two.

Figure 21B:
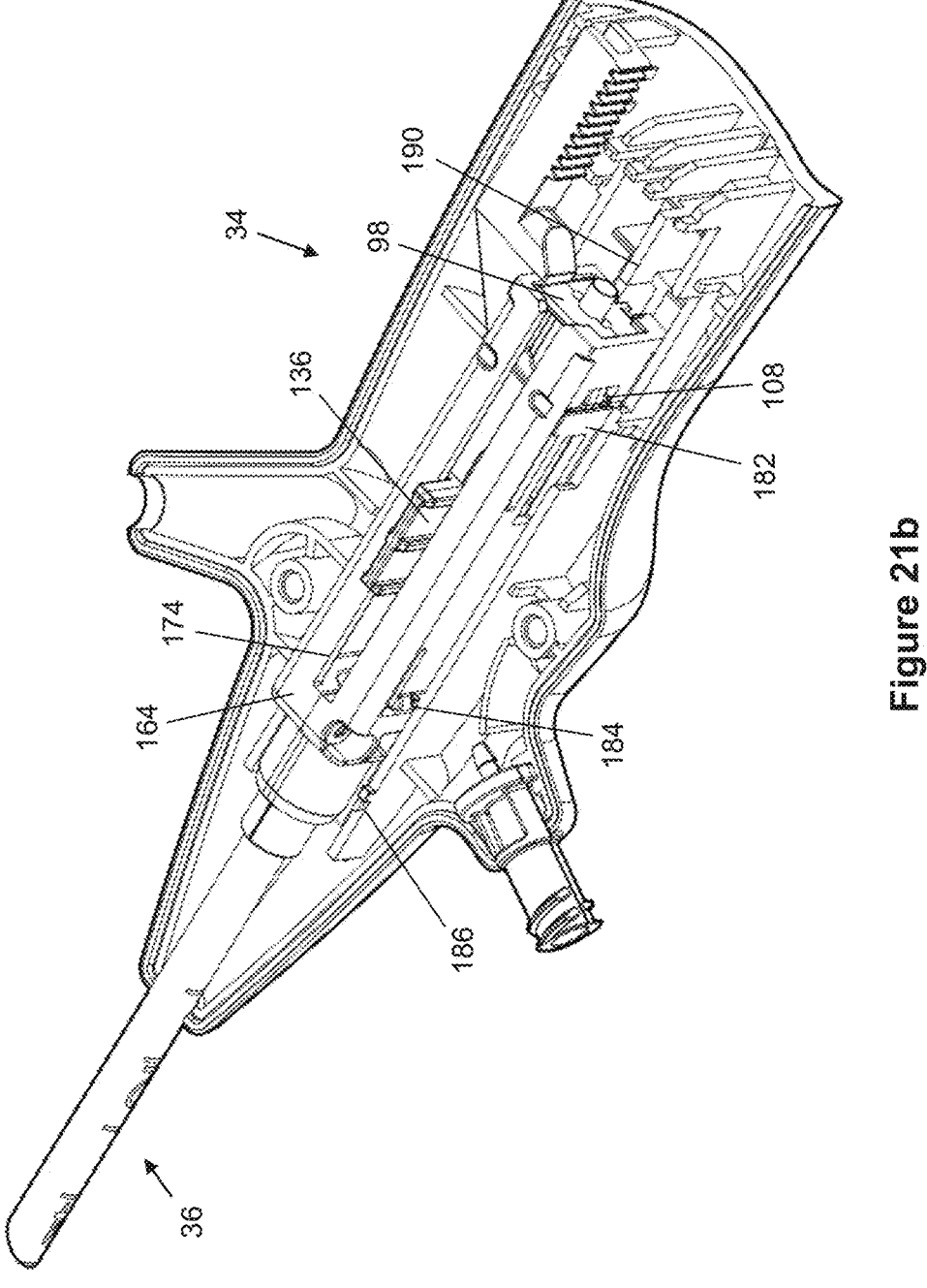
Figure 21C:
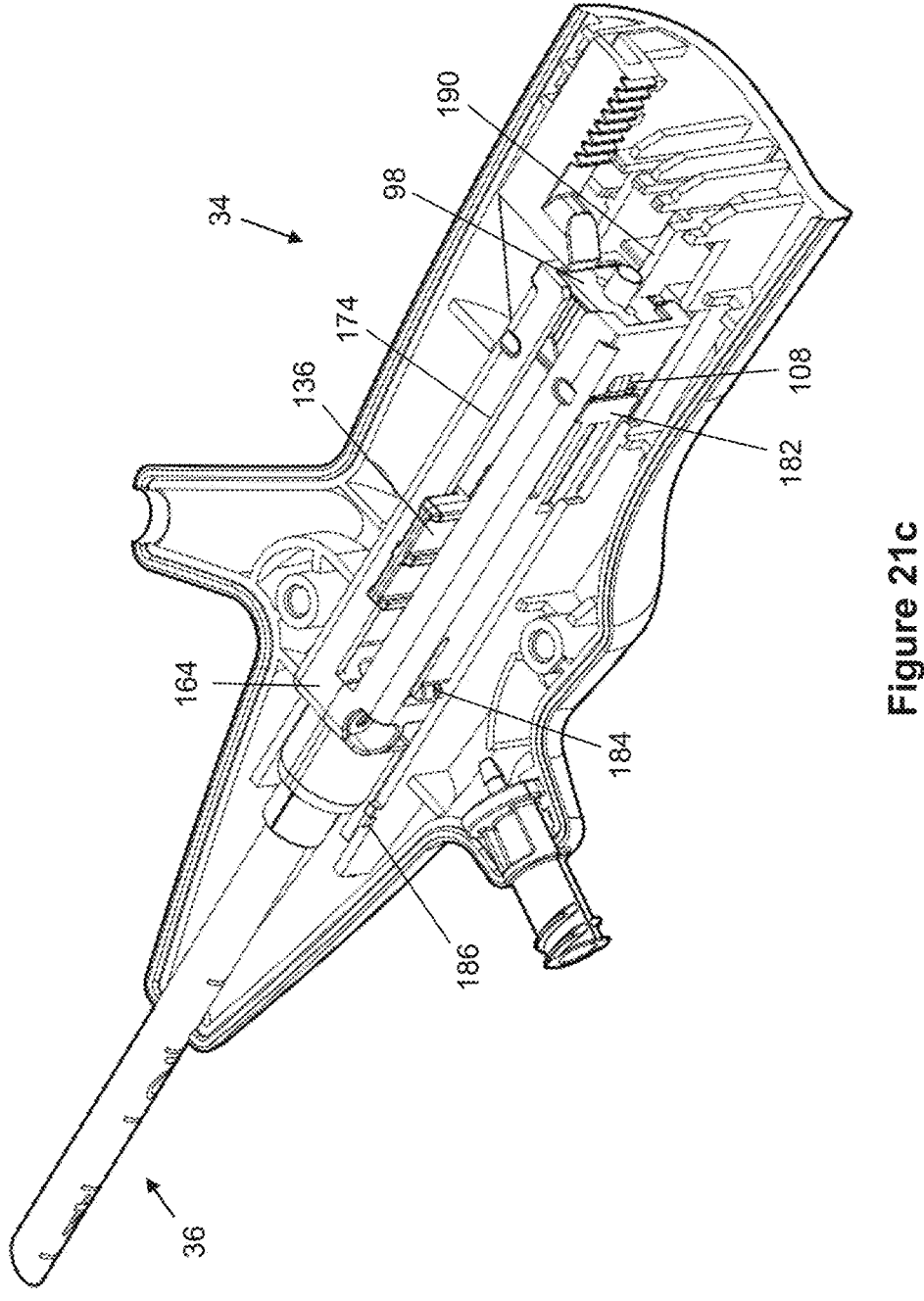
Figure 21D:
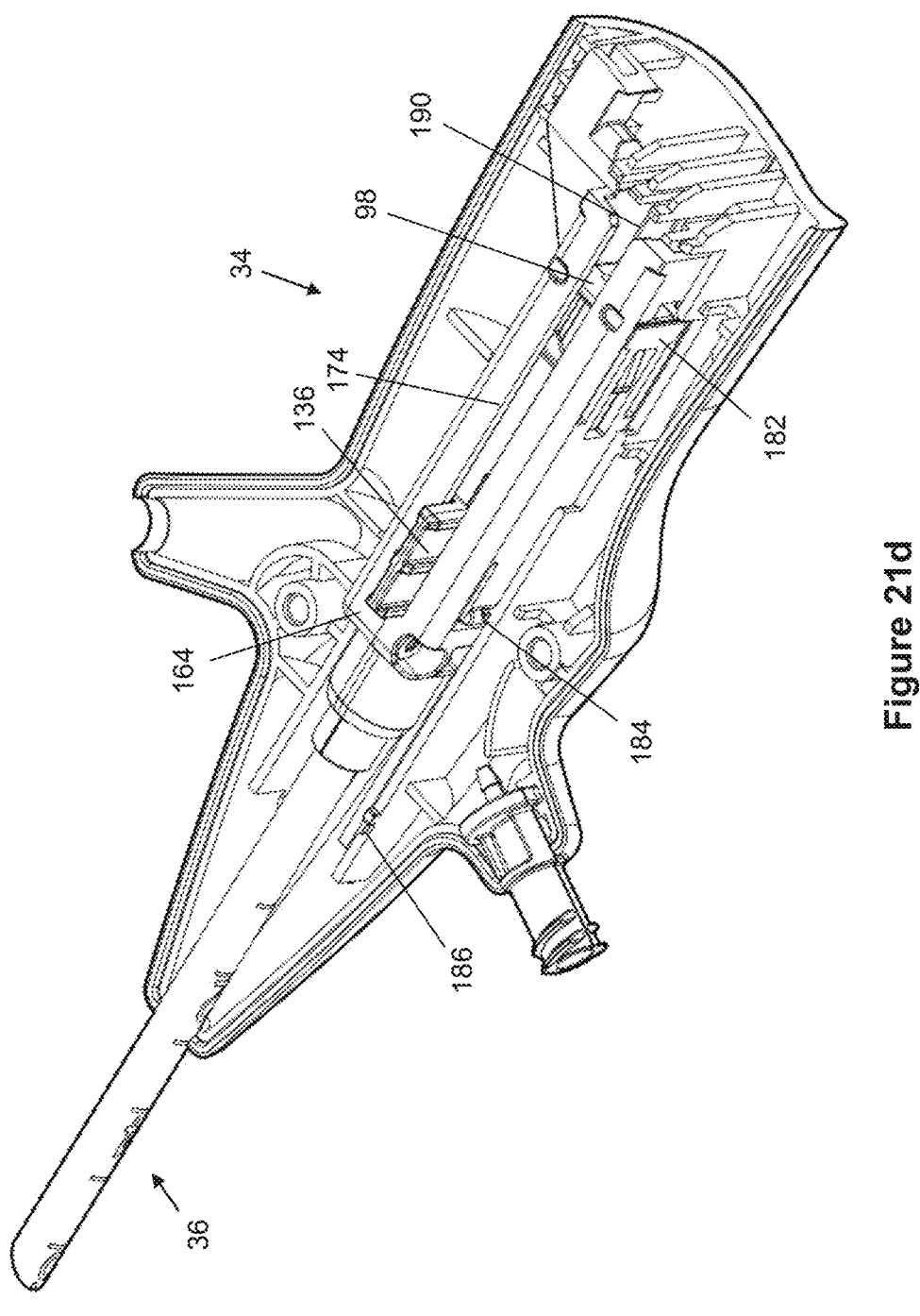
Figures 22A, 22B:
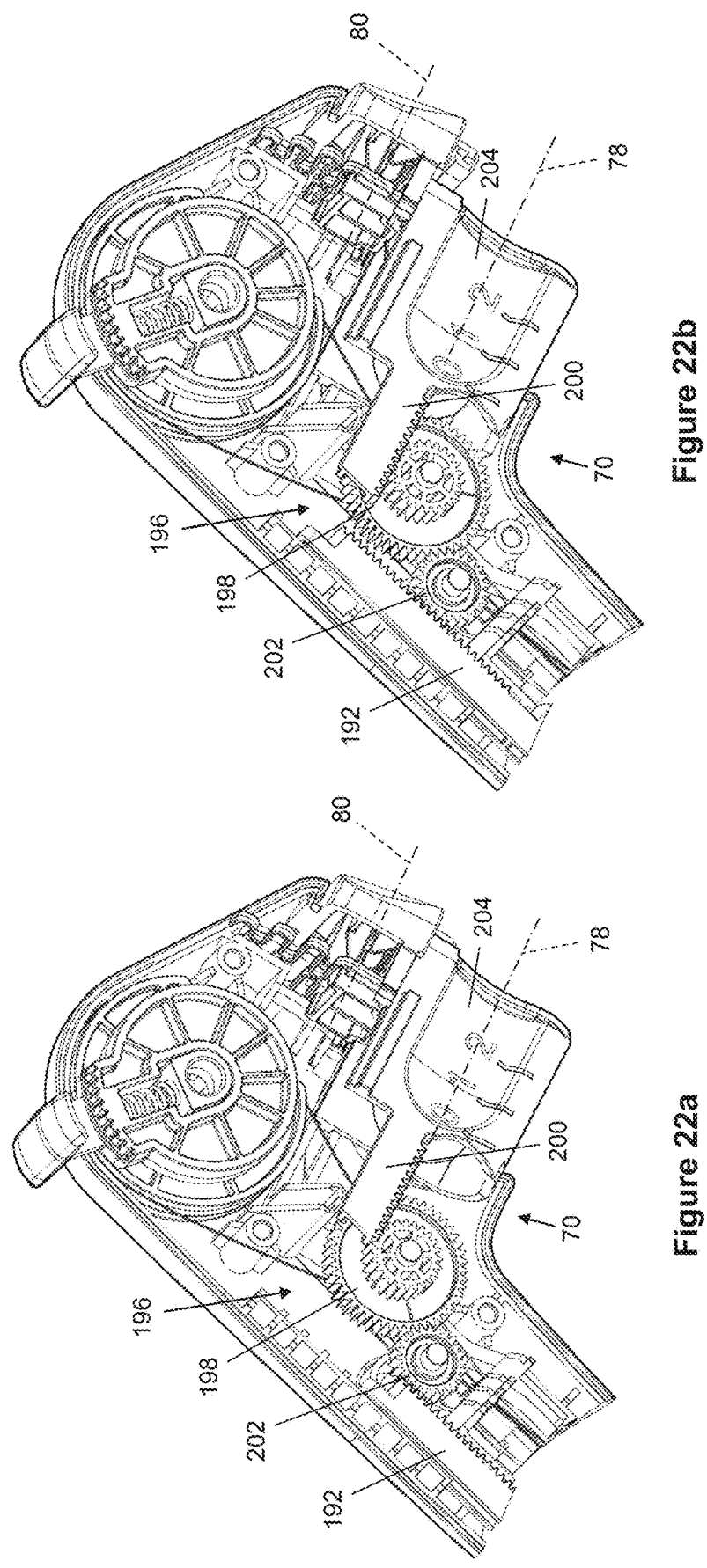
FIGS. 22*a* to 22*d* are a sequence of cut-away perspective views showing movement of external control elements relative to the housing of the handle between various deployments stages of the device.
Figures 22C, 22D:
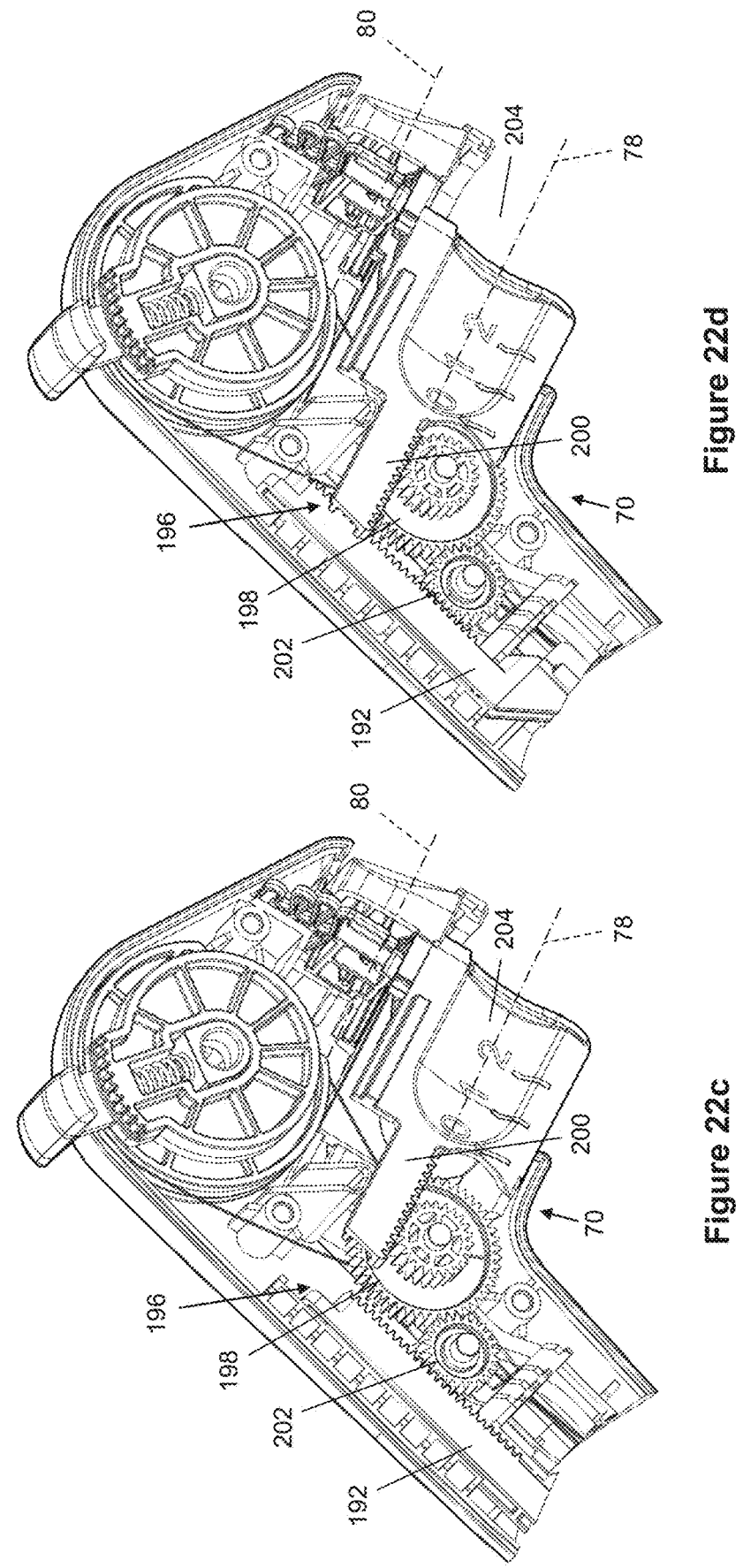

Thus, as shown in FIGS. 21*a* to 21*c*, the inner element hub 98 moves proximally with the hub casing 164 from deployment stage zero to deployment stage one. Then, as shown in FIG. 21*d*, continued proximal movement of the inner element hub 98 ceases but the hub casing 164 undergoes further proximal movement independently from, and relative to, the inner element hub 98 from deployment stage one to deployment stage two. Outward deflection of the proximal tongue 182 to clear the wedge formation 108 releases the inner element hub 98 to allow that relative movement of the hub casing 164. The proximal tongue 182 then returns resiliently inwardly to slide smoothly down the incline of the wedge formation 108 as the hub casing 164 moves proximally relative to the inner element hub 98.

The inner element hub 98 is decoupled from the hub casing 164 by using a barrier that blocks proximal movement of the inner element hub 98 but allows proximal movement of the hub casing 164 relative to the housing 62 to continue. Specifically, as shown in FIGS. 21*c* and 21*d*, proximal movement of the inner element hub 98 is blocked by encountering an integrally-moulded stop formation 190 of the housing 62. The stop formation 190 is aligned with the proximally-open longitudinal slot 174 of the hub casing 164 to be received in that slot 174 as proximal movement of the hub casing 164 continues.

As will now be explained with reference to FIGS. 22*a* to 22*d*, the deployment system 70 drives longitudinal movement of the hub casing 164 via an integral rack extension 192 (e.g., an arm) that is cantilevered from the proximal end of the body 166. Conveniently, as shown in FIGS. 19*a* and 19*b*, the rack extension 192 is moulded integrally with one of the casing parts. The rack extension 192 is offset laterally from, but otherwise extends generally parallel to, the central longitudinal axis 58 of the housing 62. An integrally-moulded rack formation 194 comprising a series of transverse teeth extends along a face of the rack extension 192 facing toward the central longitudinal axis 58.

FIGS. 22*a* to 22*d* show that the deployment system 70 comprises a transmission geartrain 196 that receives drive input from linear movement of the deployment trigger 48 along the trigger axis 78 and delivers corresponding drive output to the rack extension 192 of the hub casing 164 according to an embodiment. In one embodiment, a geartrain is a gearset. The rack extension 192 converts rotary motion of the geartrain 196 into linear movement of the hub casing 164 that faithfully follows linear movement of the deployment trigger 48, albeit in a longitudinal direction that is transverse to the trigger axis 78.

The geartrain 196 comprises an input gear 198 that is meshed with a rack 200 extending from the deployment trigger 48 parallel to the trigger axis 78. The input gear 198 is meshed with an output gear 202 that is meshed, in turn, with the rack extension 192 of the hub casing 164. The reversal of drive direction thus effected through the geartrain 196 ensures that depressing the deployment trigger 48 along the trigger axis 78 causes the hub casing 164 to move proximally within the handle 34 as the device 32 transitions from deployment stage zero to deployment stages one and two.

If a user decides to reverse the device 32 from deployment stage one back to deployment stage zero, the user simply pulls or retracts the deployment trigger 48 out of the housing 62 of the handle 34 to cause the hub casing 164 to move distally within the handle 34. For this purpose, the external part of the deployment trigger 48 has concave recesses 204 on opposite sides to help the user to grip the deployment trigger 48 between their thumb and index finger.

The overall gearing ratio of the geartrain 196 is chosen for mechanical advantage, allowing a user operating the deployment trigger 48 easily to move the hub casing 164 that acts on the outer element 38 and the inner element 40 of the delivery tube 36. The gearing ratio is also chosen for sensitivity, in that a small movement of the deployment trigger 48 along the trigger axis 78 generates a large movement of the hub casing 164 in response. This reflects that it is desirable for the device 32 to transition quickly and positively from one deployment stage to another, and therefore for the hub casing 164 not to remain for any significant period in an intermediate position when in transition between deployment stages. The detent provisions protect against inadvertent operation of the device 32 despite its deliberate sensitivity to movement of the deployment trigger 48.

Within the housing 62, as shown in FIGS. 23*a* to 23*d*, the deployment trigger 48 serving as a deployment control element comprises an integral trigger ramp 204 that faces toward the detent axis 80. The trigger ramp 204 tapers away from the detent axis 80 in an inward direction extending into the housing 62, parallel to the trigger axis 78. At an inward end of the trigger ramp 204, a base platform 206 faces toward the detent axis 80 whereas at the outward end of the trigger ramp 204, an inwardly-facing shoulder 208 extends toward the detent axis 80.

On its inward side, the detent button 60 serving as a detent release element comprises an integral follower-engagement formation being a protrusion 210 that tapers in an inward direction extending into the housing 62, parallel to the detent axis 80. The taper of the protrusion 210 defines a detent ramp 212 that faces away from the trigger axis 78.

The housing 62 contains a follower 214 that acts on, and is acted on by, the deployment trigger 48 and the detent button 60. The follower 214 is biased toward the trigger axis 78 by an integral spring 216 that acts in compression between the adjacent outer wall of the housing 62 and the follower 214. The spring 216 presses the follower 214 against the trigger ramp 204 and the detent ramp 212 in turn so that those ramps 204, 212 act successively on the follower 214 with a cam action as the deployment trigger 48 and the detent button 60 are depressed inwardly in sequence according to one embodiment.

The follower 214 has a trigger bearing edge 218 positioned to bear against the trigger ramp 204 and a detent bearing edge 220 positioned to bear against the detent ramp 212. Specifically, the trigger bearing edge 218 is at the free end of the follower 214 closest to the trigger axis 78 whereas the detent bearing edge 220 is closer to the spring 216, in this example defined by an inner edge of a window 222 that penetrates the follower 214. More specifically, the detent bearing edge 220 is on a transverse barrier member 224 of the follower that is defined in this example by an inner side of a frame around the window 222, adjoining the spring 216 of the follower 214. The window 222 is wide enough to accommodate the protrusion 210 on the inward side of the detent button 60.

Figures 23A, 23B:
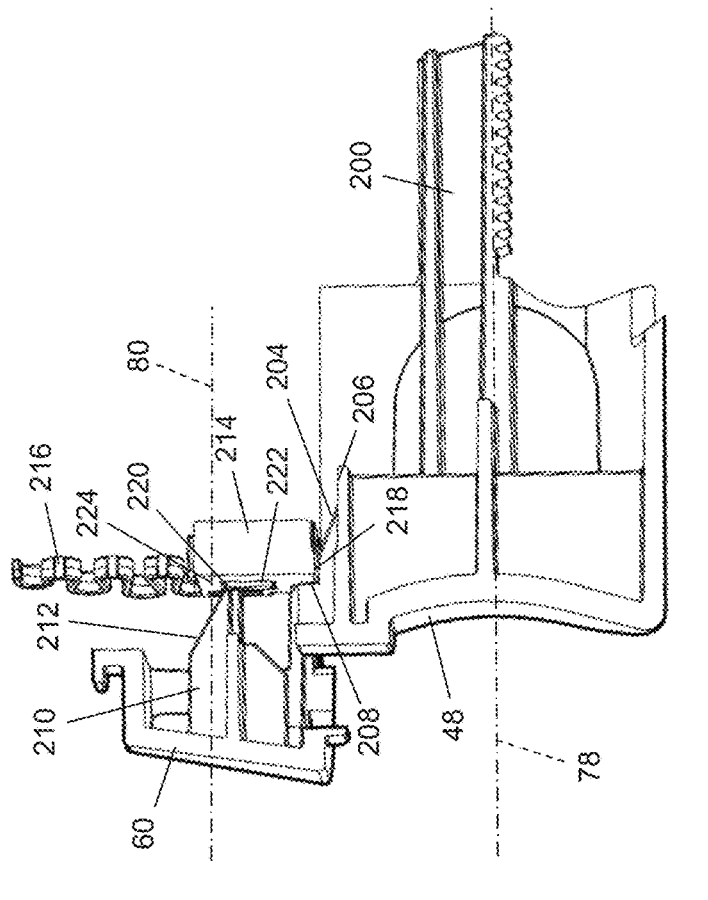
FIGS. 23*a* to 23*d* are a sequence of side views showing relative movement of, and interactions between, the control elements shown in FIGS. 22*a* to 22*d* to operate a detent function of the device.
Figure 23D:
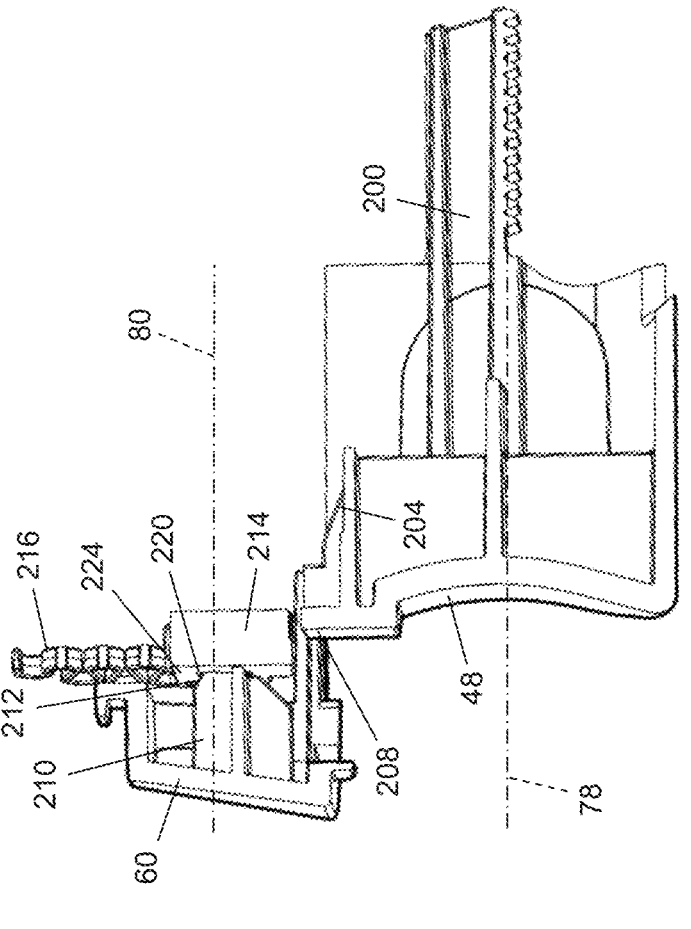
Figure 23C:
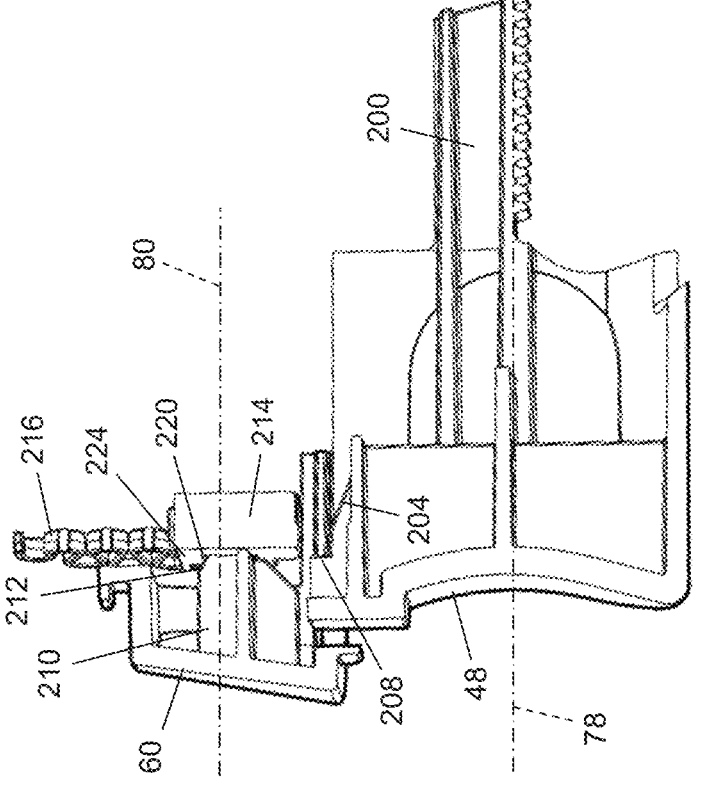

By interactions of the trigger ramp 204 and the detent ramp 212 with the trigger bearing edge 218 and the detent bearing edge 220 respectively, the follower 214 can adopt any of three positions determined by the positions of the deployment trigger 48 and the detent button 60. Specifically, the follower 214 adopts: a detent stop position when the deployment trigger 48 is in the outward position corresponding to deployment stage zero as shown in FIG. 23a; a deployment stop or trigger stop position when the deployment trigger 48 is depressed into the intermediate position corresponding to deployment stage one as shown in FIG. 23b; and a deployment release or trigger release position when the detent button 60 is depressed at deployment stage one as shown in FIG. 23c. This allows further inward movement of the deployment trigger 48 to the fully inward position corresponding to deployment stage two, as shown in FIG. 23d. Movements of the follower 214 from the detent stop position to the intermediate trigger stop position and from there to the trigger release position all take place against the bias of the spring 216.

Thus, inward movement of the deployment trigger 48 to bring the device 32 to deployment stage one moves the follower 214 to the trigger stop position shown in FIG. 23a at which further inward movement of the deployment trigger 48 is blocked but inward movement of the detent button 60 is enabled. Thus, the trigger stop position can also be regarded as a detent release position. Inward movement of the detent button 60 then moves the follower 214 to the trigger release position that enables further inward movement of the deployment trigger 48 to transition the device 32 from deployment stage one to deployment stage two.

Specifically, when the deployment trigger 48 is in an outward position corresponding to deployment stage zero, the trigger bearing edge 218 of the follower 214 rests against the base platform 206 at the inward end of the trigger ramp 204 as shown in FIG. 23a. The barrier member 224 of the follower 214 is then aligned with the protrusion 210 of the detent button 60 to block inward movement of the detent button 60.

When the deployment trigger 48 is depressed inwardly toward an inward position corresponding to deployment stage one as shown in FIG. 23b, the trigger ramp 204 slides past the trigger bearing edge 218 of the follower 214 and thereby forces the follower 214 away from the trigger axis 78 against the bias of the spring 216. Inward movement of the deployment trigger 48 continues until the follower 214 encounters the shoulder 208 at the outward end of the trigger ramp 204, at a position of the deployment trigger 48 corresponding to deployment stage one. Interaction between the follower 214 and the shoulder 208 initially prevents further inward movement of the deployment trigger 48 beyond deployment stage one.

Movement of the follower 214 away from the trigger axis 78 under the action of the trigger ramp 204 moves the barrier member 224 of the follower 214 out of alignment with the protrusion 210 of the detent button 60, and conversely brings the window 222 of the follower 214 into alignment with the protrusion 210 of the detent button 60. This enables inward movement of the detent button 60 as the protrusion 210 is received in the window 222.

As the protrusion 210 of the detent button 60 enters the window 222 of the follower 214, the detent ramp 212 comes into contact with the detent bearing edge 220 on the transverse barrier member 224 that defines the inner edge of the window 222. Continued inward movement of the detent button 60 causes the detent ramp 212 to slide past the detent bearing edge 220 and so forces the follower 214 further away from the trigger axis 78 against the bias of the spring 216. This further movement of the follower 214 frees the follower 214 from the shoulder 208 at the outward end of the trigger ramp 204, thus enabling further inward movement of the deployment trigger 48 beyond deployment stage one into deployment stage two.

If movement of the deployment trigger 48 is reversed to return the device 32 from deployment stage one to deployment stage zero, the follower 214 returns to its initial position in which the trigger bearing edge 218 of the follower 214 rests against the base platform 206 at the inward end of the trigger ramp 204. The barrier member 224 of the follower 214 is then aligned again with the protrusion 210 of the detent button 60 to block inward movement of the detent button 60.

Thus, the detent button 60 enables movement of the deployment trigger 48 into deployment stage two by virtue of being enabled by movement of the deployment trigger 48 from deployment stage zero to deployment stage one. Inward movement of the deployment trigger 48 to bring the device 32 to deployment stage one moves the follower 214 against the bias of the spring 216. That movement enables inward movement of the detent button 60. Inward movement of the detent button 60 enables further inward movement of the deployment trigger 48 to transition the device 32 from deployment stage one to deployment stage two.

Figures 24A, 24B:
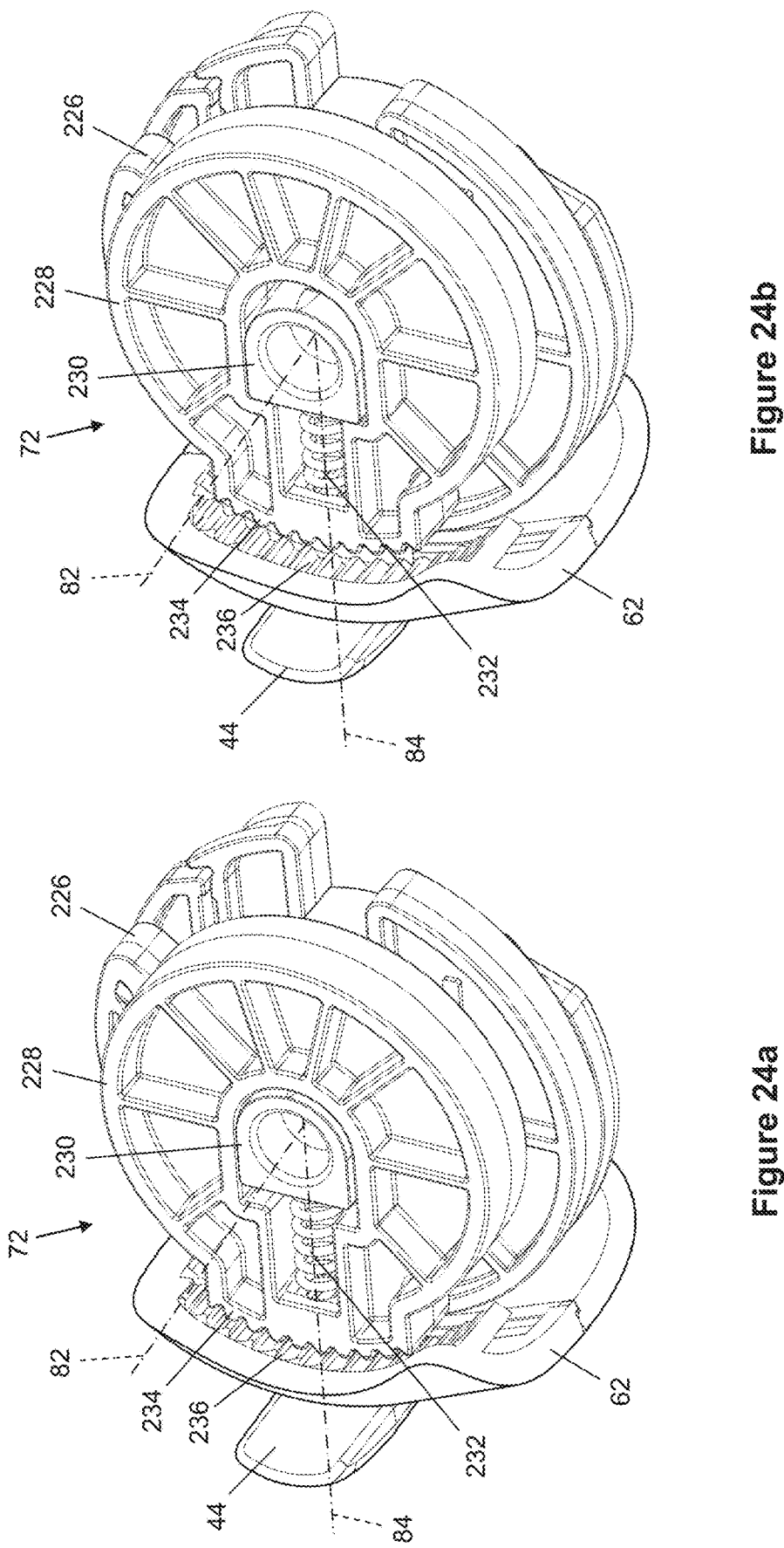
FIGS. 24*a* and 24*b* are perspective views showing operation of a steering mechanism of the device.

Turning finally to FIGS. 24a and 24b, the steering lever 44 of the steering system 72 acts on a steering dial 226 that pivots about the pivot axis 82 within the housing 62. Steering wires (not shown) extend distally from respective opposed sides of the steering dial 226 and are crimped to the corresponding steering wires 106 that extend proximally from the intermediate element hub 100. Pivoting the steering dial 226 under angular forces applied via the steering lever 44 thereby applies tension selectively to the steering wires 106 to deflect the steering sheath 94 of the delivery tube 36 as described previously.

At its inward end within the housing 62, the steering lever 44 comprises an integral yoke 228 that surrounds the pivot axis 82 of the steering lever 44. The aforementioned locking axis 84, being a longitudinal axis of the steering lever 44, extends along a radius that intersects the pivot axis 82.

The yoke 228 surrounds, and is engaged with, a complementary hub spigot 230 of the steering dial 226. The yoke 228 is oversized relative to the hub spigot 230 parallel to the locking axis 84 whereas in directions transverse to that axis 84, the hub spigot 230 is a close sliding fit within the yoke 228. Specifically, parallel side facets of the hub spigot 230 bear against opposed side limbs of the yoke 228 to lock the yoke 228 against angular movement relative to the hub spigot 230. Consequently, torque transmitted from angular movement of the lever 44, for example when operated by a user's thumb, turns the dial 226 about the pivot axis 82. Conversely, the yoke 228 is able to reciprocate to a limited extent in directions parallel to the locking axis 84. In that case, the side facets of the hub spigot 230 slide within the opposed side limbs of the yoke 228.

A spring 232 surrounds the locking axis 84 on an outboard side of the pivot axis 82 and acts in compression between the yoke 228 and the hub spigot 230 to bias the steering lever 44 outwardly along the locking axis 84. Thus, a user's thumb can press the steering lever 44 inwardly into the housing 62 in translation against the bias of the spring 232 to unlatch the steering lever 44 for angular movement. When inward thumb pressure is released, the bias of the spring 232 returns the steering lever 44 to an outward position in which the steering lever 44 is latched to prevent inadvertent angular movement.

For the purpose of latching the steering lever 44, the yoke 228 comprises latch formations that face outwardly along the locking axis 84. The latch formations are exemplified here by a convex-curved array 234 of teeth that is opposed to a complementary concave-curved array 236 of teeth facing inwardly from an inner face of the housing 62.

The arrays 234, 236 of teeth are each curved along their length with a substantially constant radius of curvature centred on the pivot axis 82. The teeth of the arrays 234, 236 are spaced apart along the length of the arrays 234, 236 and so are angularly spaced about the pivot axis 82. In this example, the teeth are oriented orthogonally with respect to the length of the respective arrays 234, 236. Elegantly, as shown here, the concave-curved array 236 of teeth facing inwardly from the housing 62 is integrally moulded with one or both of the shells 64 of the housing 62, which have corresponding curvature about the pivot axis 82.

When the steering lever 44 is released, the bias of the spring 232 urges the latch formations of the yoke 228 outwardly, together with the yoke 228, to engage with teeth of the inwardly-facing array 236 that correspond to the angular position of the steering lever 44. This latches the steering lever 44 at a desired angular position. Conversely, depressing the steering lever 44 against the bias of the spring 232 releases the latch formations from the teeth of the inwardly-facing array 236 to unlatch the steering lever 44 for angular movement.

Many other variations are possible within the inventive concept. For example: the device could comprise an on-board power supply; imaging could be effected by a non-digital imaging system other than a chip, such as by conveying images along a fibre-optic bundle; the stiffness of the imaging sheath can be tailored to vary along its length—for example, with tailored braiding comprising braided or coiled elements of varying density, pitch, angle and/or thickness and polymer durometer—so as to provide stable support for the implant and yet to navigate easily within the deflected steering sheath.

In the example shown, the implant holding feature is the moulded steering tip component that accommodates the steering ring as a separate component. However, in another embodiment, the implant holding feature and a pull ring or other steering formation could instead be integrated into one component.

The ramp formations of the deployment trigger and the detent button could instead, or additionally, be provided on the follower.

Changes and modifications in the embodiments described herein can be carried out without departing from the principles of the present disclosure. Each of the disclosed aspects and examples of the present disclosure may be considered individually or in combination with other aspects, examples, and variations of the disclosure.

While the methods, devices and systems described herein may be susceptible to various modifications and alternative forms, specific examples thereof have been shown in the drawings and are herein described in detail. Embodiments are not to be limited to the particular forms or methods disclosed, but rather intended is to cover modifications, equivalents and alternatives falling within the spirit and scope of the various examples and embodiments described herein and/or in the claims. Further, the disclosure herein of any particular feature, aspect, method, property, characteristic, quality, attribute, element or the like in connection with an example can be used in all other examples and embodiments set forth herein. In addition, unless otherwise specified, none of the steps of the methods of the present disclosure are confined to any particular order of performance. Any methods disclosed herein need not be performed in the order recited. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some examples may be performed using the sequence of operations described herein, while other examples may be performed following a different sequence of operations.

Conditional language used herein, such as, among others, "can," "might," "may," "e.g.," and the like, unless specifically stated otherwise, or otherwise understood within the context as used, is generally intended to convey that some examples include, while other examples do not include, certain features, elements, and/or states. Thus, such conditional language is not generally intended to imply that features, elements, blocks, and/or states are in any way required for one or more examples or that one or more examples necessarily include logic for deciding, with or without author input or prompting, whether these features, elements and/or states are included or are to be performed in any particular example. Where devices or methods "comprise" or "include" (these two open terms can be used interchangeably) certain features or steps, such devices or methods may also "consist essentially of" or "consist of" such features or steps if expressly identified as such in the claims.

The methods disclosed herein may include certain actions taken by a practitioner; however, the methods can also include any user or third-party instruction of those actions, either expressly or by implication. For example, actions such as "positioning a device" include "instructing positioning of a device."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonable under the circumstances, for example ±5%, ±10%, ±15%, etc.). For example, "about 4 mm" includes "4 mm." Phrases preceded by a term such as "substantially" include the recited phrase and should be interpreted based on the circumstances (e.g., as much as reasonably possible under the circumstances). For example, "substantially linear" includes "linear." Unless stated otherwise, all measurements are at standard conditions including temperature and pressure. The phrase "at least one of" is intended to require at least one item from the subsequent listing, not one type of each item from each item in the subsequent listing. For example, "at least one of A, B, and C" can include A; B; C; A and B; A and C; B and C; or A, B, and C.

What is claimed is:

1. A deployment system for deploying an implant in a patient's body, the system comprising:
   a deployment control element that is movable along a trigger axis;
   a trigger ramp that is movable with the deployment control element and inclined relative to the trigger axis;

a deployment drive that is operable in response to movement of the deployment control element along the trigger axis from a first position in which the implant is undeployed, to a second position in which the implant is partially deployed, and to a third position in which the implant is fully deployed; and a detent mechanism that is configured to block movement of the deployment control element from the second position to the third position, wherein the detent mechanism comprises:

a follower that is movable along a follower axis, transverse to the trigger axis, by a cam action of the trigger ramp driven by movement of the deployment control element from the first position to the second position, wherein the follower is movable along the follower axis from a detent stop position into a deployment stop position at which the follower blocks further movement of the deployment control element into the third position;

a detent release element that is movable along a detent axis from a lock position into an unlock position when enabled by movement of the follower into a detent release position;

a detent ramp that is movable with the detent release element and inclined relative to the detent axis; and a protrusion that is movable with the detent release element, wherein in the detent stop position a barrier member of the follower is in blocking opposition to the protrusion to prevent movement of the detent release element into the unlock position and in the detent release position an opening of the follower is in receiving opposition to the protrusion to permit movement of the detent release element into the unlock position, said movement of the detent release element acting on the follower by a cam action of the detent ramp to move the follower further along the follower axis from the deployment stop position into a deployment release position at which the follower frees the deployment control element for movement from the second position to the third position.

2. The system of claim 1, wherein the detent release position of the follower corresponds to the deployment stop position of the follower.

3. The system of claim 1, wherein the follower is in the detent stop position when the deployment control element is in the first position.

4. The system of claim 1, wherein the follower is biased toward the detent stop position.

5. The system of claim 1, wherein the follower is movable against a bias into the deployment stop position and the deployment release position.

6. The system of claim 1, wherein the detent release element adjoins the deployment control element.

7. The system of claim 1, wherein the detent axis is substantially parallel to the trigger axis.

8. The system of claim 1, wherein the trigger ramp is shaped to engage the follower when the deployment control element reaches the second position, thereby blocking further movement of the deployment control element toward the third position.

9. The system of claim 8, wherein the trigger ramp comprises a shoulder that extends transversely relative to an inclined surface of the trigger ramp and that is opposed to the follower.

10. The system of claim 1, wherein the deployment control element comprises grip formations arranged to facilitate gripping and pulling the deployment control element outwardly from the second position to the first position.

11. A deployment system for deploying an implant in a patient's body, the system comprising:

a deployment control element that is movable along a trigger axis;

a trigger ramp that is movable with the deployment control element and inclined relative to the trigger axis;

a deployment drive that is operable in response to movement of the deployment control element along the trigger axis from a first position in which the implant is undeployed, to a second position in which the implant is partially deployed, and to a third position in which the implant is fully deployed; and a detent mechanism that is configured to block movement of the deployment control element from the second position to the third position, wherein the detent mechanism comprises:

a follower that is movable along a follower axis, transverse to the trigger axis, by a cam action of the trigger ramp driven by movement of the deployment control element from the first position to the second position, wherein the follower is movable along the follower axis from a detent stop position into a deployment stop position at which the follower blocks further movement of the deployment control element into the third position;

a detent release element that is movable along a detent axis from a lock position into an unlock position when enabled by movement of the follower into a detent release position; and a detent ramp that is movable with the detent release element and inclined relative to the detent axis;

wherein in the detent stop position, the follower prevents movement of the detent release element into the unlock position and in the detent release position the follower permits movement of the detent release element into the unlock position, said movement of the detent release element acting on the follower by a cam action of the detent ramp to move the follower further along the follower axis from the deployment stop position into a deployment release position at which the follower frees the deployment control element for movement from the second position to the third position.

12. The system of claim 11, further comprising a protrusion that is movable with the detent release element, and wherein: the follower comprises a barrier member that is in blocking opposition to the protrusion when the follower is in the detent stop position, to prevent movement of the detent release element into the unlock position; and the follower further comprises an opening that is in receiving opposition to the protrusion when the follower is in the detent release position, to permit movement of the detent release element into the unlock position.

13. The system of claim 12, wherein the barrier member and the opening of the follower are disposed in succession along the follower axis.

14. The system of claim 11, wherein the detent release position of the follower corresponds to the deployment stop position of the follower.

15. The system of claim 11, wherein the follower is biased into the detent stop position when the deployment control element is in the first position, and is movable against that bias into the deployment stop position and the deployment release position.

16. The system of claim 11, wherein the detent release element adjoins the deployment control element.

17. The system of claim 11, wherein the detent axis is substantially parallel to the trigger axis.

18. The system of claim 11, wherein the trigger ramp is shaped to engage the follower when the deployment control element reaches the second position, thereby blocking further movement of the deployment control element toward the third position.

19. The system of claim 18, wherein the trigger ramp comprises a shoulder that extends transversely relative to an inclined surface of the trigger ramp and that is opposed to the follower.

20. The system of claim 19, wherein movement of the follower into the deployment release position disengages the follower from the trigger ramp by moving the follower clear of the shoulder.

\* \* \* \* \*